(12) United States Patent
Dees, Jr. et al.

(10) Patent No.: US 8,834,473 B2
(45) Date of Patent: Sep. 16, 2014

(54) LOCKABLE ORIENTATION INSTRUMENT ASSEMBLY

(75) Inventors: Roger Ryan Dees, Jr., Senatobia, MS (US); Jeffrey Andrew Sharp, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 358 days.

(21) Appl. No.: 12/728,490

(22) Filed: Mar. 22, 2010

(65) Prior Publication Data

US 2010/0234850 A1 Sep. 16, 2010

Related U.S. Application Data

(63) Continuation-in-part of application No. 11/344,778, filed on Feb. 1, 2006, now Pat. No. 7,682,362.

(60) Provisional application No. 60/649,059, filed on Feb. 1, 2005.

(51) Int. Cl.
*A61B 17/58* (2006.01)
*A61B 17/15* (2006.01)
*A61B 17/17* (2006.01)
*A61B 19/00* (2006.01)

(52) U.S. Cl.
CPC .......... *A61B 17/155* (2013.01); *A61B 17/1764* (2013.01); *A61B 2019/266* (2013.01)
USPC ............... 606/86 R; 606/88; 33/512; 600/587

(58) Field of Classification Search
USPC ................ 81/9.2; 33/511–515; 600/587–595; 606/86 R, 87–89, 102, 130; 403/325, 403/240; 24/458
See application file for complete search history.

(56) References Cited

U.S. PATENT DOCUMENTS

| | | | |
|---|---|---|---|
| 2,309,502 | A | 1/1943 | Douglas |
| 3,949,643 | A | 4/1976 | Mucci et al. |
| 4,393,868 | A | 7/1983 | Teague |
| 4,471,993 | A | 9/1984 | Watson |

(Continued)

FOREIGN PATENT DOCUMENTS

| | | |
|---|---|---|
| DE | 198528770 | 1/1986 |
| WO | WO9730640 | 8/1997 |
| WO | WO9925263 | 5/1999 |

OTHER PUBLICATIONS

International Search Report and Written Opinion for International Application No. PCT/US2011/029321 mailed Nov. 25, 2011, 12 pages.

(Continued)

*Primary Examiner* — Eduardo C Robert
*Assistant Examiner* — Julianna N Harvey
(74) *Attorney, Agent, or Firm* — Fish & Richardson, P.C.

(57) ABSTRACT

Disclosed are lockable instrument assemblies for quick and easy configuration of surgical instrumentation. The assemblies are operable between a locked and unlocked position, and generally include an aperture having a shaped profile which receives an adjustment member therein. When the assemblies are placed in a locked assembly configuration, the adjustment member is prevented from rotating or translating within the aperture. When the assemblies are placed in an unlocked assembly configuration, the adjustment member is permitted to rotate or translate within the aperture. Also disclosed are methods of using and making lockable instrument assemblies.

22 Claims, 21 Drawing Sheets

(56) References Cited

U.S. PATENT DOCUMENTS

| | | |
|---|---|---|
| RE31,809 E | 1/1985 | Danieletto et al. |
| 4,604,997 A | 8/1986 | De Bastiani et al. |
| 4,736,742 A | 4/1988 | Alexson et al. |
| 4,834,092 A | 5/1989 | Alexson et al. |
| 4,887,865 A | 12/1989 | Dawidzon |
| 4,936,843 A | 6/1990 | Sohngen |
| 4,952,213 A | 8/1990 | Bowman et al. |
| 4,976,713 A | 12/1990 | Landanger et al. |
| 5,003,965 A | 4/1991 | Talish et al. |
| 5,035,700 A | 7/1991 | Kenna |
| 5,049,151 A | 9/1991 | Durham et al. |
| 5,053,037 A | 10/1991 | Lackey |
| 5,305,203 A | 4/1994 | Raab |
| 5,330,501 A | 7/1994 | Tovey et al. |
| 5,360,431 A | 11/1994 | Puno et al. |
| 5,368,549 A | 11/1994 | McVicker |
| 5,454,810 A | 10/1995 | Pohl et al. |
| 5,456,655 A | 10/1995 | Morris |
| 5,462,550 A | 10/1995 | Dietz et al. |
| 5,484,446 A | 1/1996 | Burke et al. |
| 5,549,703 A | 8/1996 | Daigle et al. |
| 5,556,374 A | 9/1996 | Grace et al. |
| 5,658,292 A | 8/1997 | Axelson |
| 5,667,507 A | 9/1997 | Corin et al. |
| 5,674,225 A | 10/1997 | Muller |
| 5,683,397 A | 11/1997 | Vendrely et al. |
| 5,697,158 A | 12/1997 | Klinzing et al. |
| 5,700,268 A | 12/1997 | Bertin |
| 5,711,297 A | 1/1998 | Iliff |
| 5,725,532 A | 3/1998 | Shoemaker |
| 5,748,767 A | 5/1998 | Raab |
| 5,827,208 A | 10/1998 | Mason et al. |
| 5,910,143 A | 6/1999 | Cripe et al. |
| 5,928,234 A | 7/1999 | Manspeizer |
| 5,980,475 A | 11/1999 | Gibbons |
| 6,027,507 A | 2/2000 | Anderson et al. |
| 6,077,270 A | 6/2000 | Katz |
| 6,139,548 A | 10/2000 | Errico |
| 6,162,228 A | 12/2000 | Durham |
| 6,162,234 A | 12/2000 | Freedland et al. |
| 6,168,595 B1 | 1/2001 | Durham et al. |
| 6,175,979 B1 | 1/2001 | Jackson |
| 6,193,724 B1 | 2/2001 | Chan |
| RE37,338 E | 8/2001 | McVicker |
| 6,290,704 B1 | 9/2001 | Burkinshaw et al. |
| 6,300,941 B1 | 10/2001 | Segalle |
| 6,344,043 B1 | 2/2002 | Pappas |
| 6,402,756 B1 | 6/2002 | Ralph et al. |
| 6,436,058 B1 | 8/2002 | Krahner et al. |
| 6,447,548 B1 | 9/2002 | Ralph et al. |
| 6,532,002 B2 | 3/2003 | Segalle |
| 6,554,864 B2 | 4/2003 | Ralph et al. |
| 6,558,423 B1 | 5/2003 | Michelson |
| 6,575,980 B1 | 6/2003 | Robie et al. |
| 6,595,936 B1 | 7/2003 | Oladipo |
| 6,595,994 B2 | 7/2003 | Kilpela et al. |
| 6,605,092 B2 | 8/2003 | Grumberg et al. |
| 6,666,867 B2 | 12/2003 | Ralph et al. |
| 6,673,114 B2 | 1/2004 | Hartdegen et al. |
| 6,689,134 B2 | 2/2004 | Ralph et al. |
| 6,712,823 B2 | 3/2004 | Grusin et al. |
| 6,729,794 B2 | 5/2004 | Callaway et al. |
| 6,746,453 B2 | 6/2004 | Deloge et al. |
| 6,837,904 B2 | 1/2005 | Ralph et al. |
| 6,890,356 B2 | 5/2005 | Ralph et al. |
| 6,916,325 B2 | 7/2005 | Kana et al. |
| 6,925,339 B2 | 8/2005 | Grimm et al. |
| 6,951,561 B2 | 10/2005 | Warren et al. |
| 6,974,483 B2 | 12/2005 | Murray |
| 6,991,802 B1 | 1/2006 | Ahola et al. |
| 7,001,346 B2 | 2/2006 | White |
| 7,008,422 B2 | 3/2006 | Foley et al. |
| 7,041,135 B2 | 5/2006 | Michelson |
| 7,601,155 B2 | 10/2009 | Petersen |
| 7,618,420 B2 | 11/2009 | Collazo |
| 7,682,362 B2 | 3/2010 | Dees, Jr. |
| 2002/0173797 A1 | 11/2002 | Van Zile et al. |
| 2003/0040752 A1 | 2/2003 | Kitchens |
| 2003/0114859 A1 | 6/2003 | Brusin et al. |
| 2003/0149378 A1* | 8/2003 | Peabody et al. ............. 600/587 |
| 2003/0153924 A1 | 8/2003 | Kana et al. |
| 2004/0039395 A1 | 2/2004 | Coon et al. |
| 2005/0049603 A1 | 3/2005 | Calton et al. |
| 2005/0149042 A1 | 7/2005 | Metzger |
| 2005/0203528 A1 | 9/2005 | Couture et al. |
| 2005/0261696 A1 | 11/2005 | Overes et al. |
| 2005/0273115 A1 | 12/2005 | Coon et al. |
| 2006/0179979 A1 | 8/2006 | Dees |
| 2008/0183178 A1 | 7/2008 | Collazo |
| 2009/0204115 A1 | 8/2009 | Dees et al. |

OTHER PUBLICATIONS

Brochure entitled Genesis II® Total Knee System Primary Surgical Technique by Smith & Nephew, 36 pages (1998).
Femoral Anterior Stylus schematic described as 'Lock knob (threaded) which locks arm from all movement,' one page (1997).
Revision Tibial Stylus schematic, one page (2004).
Schematic described as 'Spring and nylon washer provide resistance to the stylus arm to provide resistance to translation, yet allows it when force is applied,' one page (2003).
Anterior Stylus Assembly schematic described as 'This stylus only allows rotation of the stylus arm around the connection axis,' one page (1996).
Notice of Allowance from U.S. Appl. No. 11/344,778 dated Nov. 6, 2009.
Examiner's Interview Summary Record from U.S. Appl. No. 11/344,778 dated Nov. 4, 2009.
Examiner's Interview Summary Record from U.S. Appl. No. 11/344,778 dated Nov. 2, 2009.
Office Action from U.S. Appl. No. 11/344,778 dated Aug. 17, 2009.
Office Action from U.S. Appl. No. 11/344,778 dated Mar. 3, 2009.
Office Action from U.S. Appl. No. 11/344,778 dated Dec. 8, 2008.
International Search Report for International Application No. PCT/US2006/038859, mailed Feb. 2, 2007, 3 pages.
Examiner's First Report for corresponding Australian Application No. 2006299438, mailed Sep. 8, 2011, 3 pages.
Office Action for corresponding Japanese Application No. 2008-534670, mailed Aug. 9, 2011, 4 pages.
Notice of Reasons for Rejection for Japanese Application No. 2008-534670, mailed Apr. 3, 2012.
Examination Report issued in Canadian Application No. 2,624,644, on Mar. 19, 2013, 3 pages.
Communication Pursuant to Article 94(3) EPC for European Application No. 06816263.5, mailed Jun. 6, 2013.

* cited by examiner

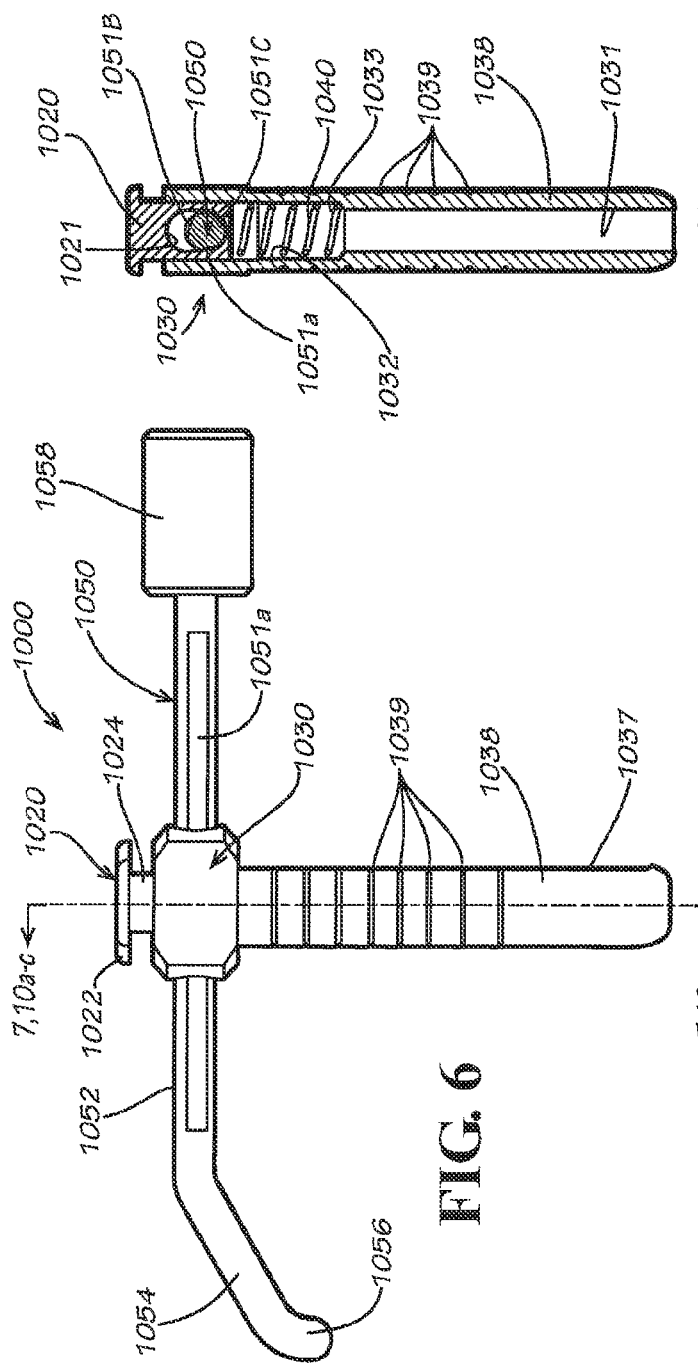

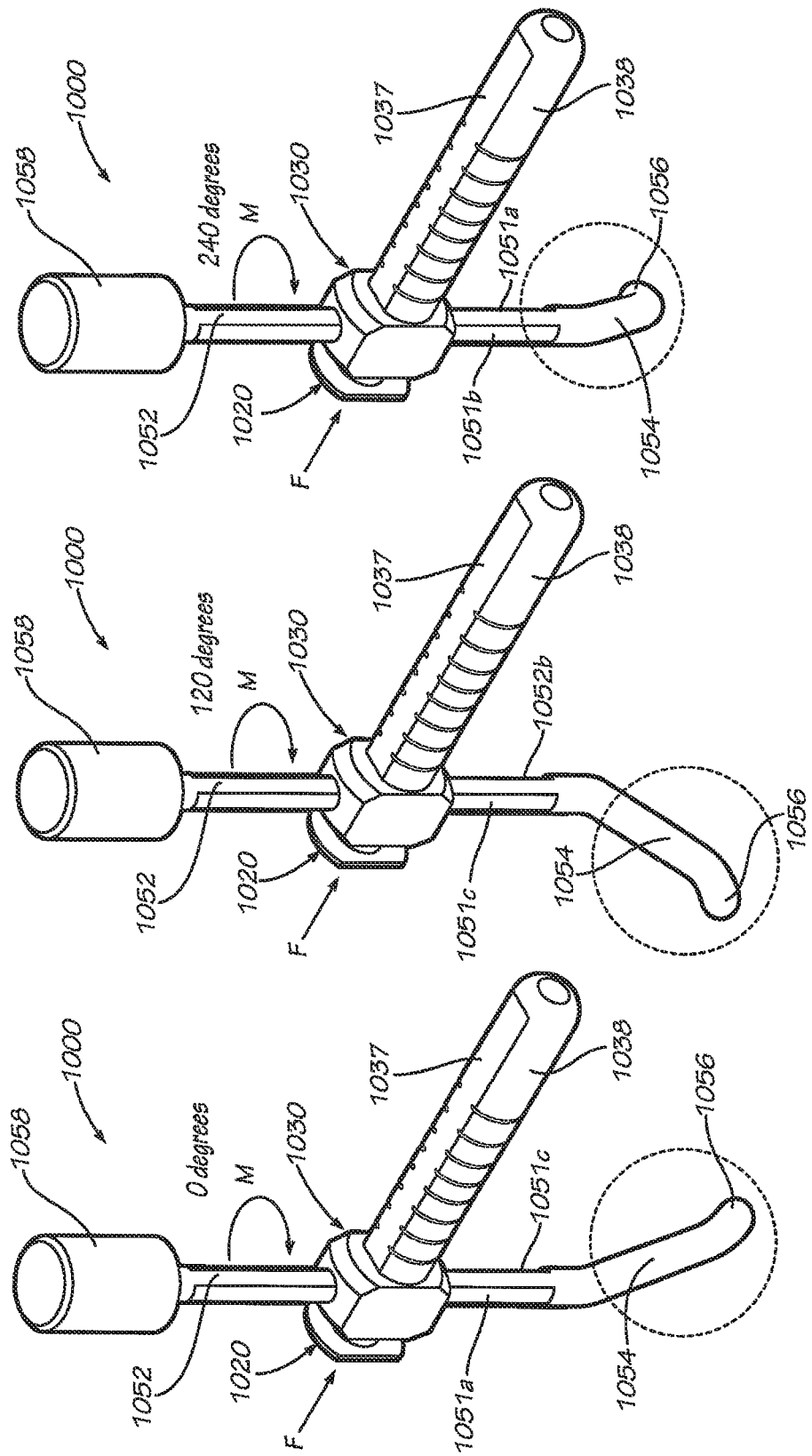

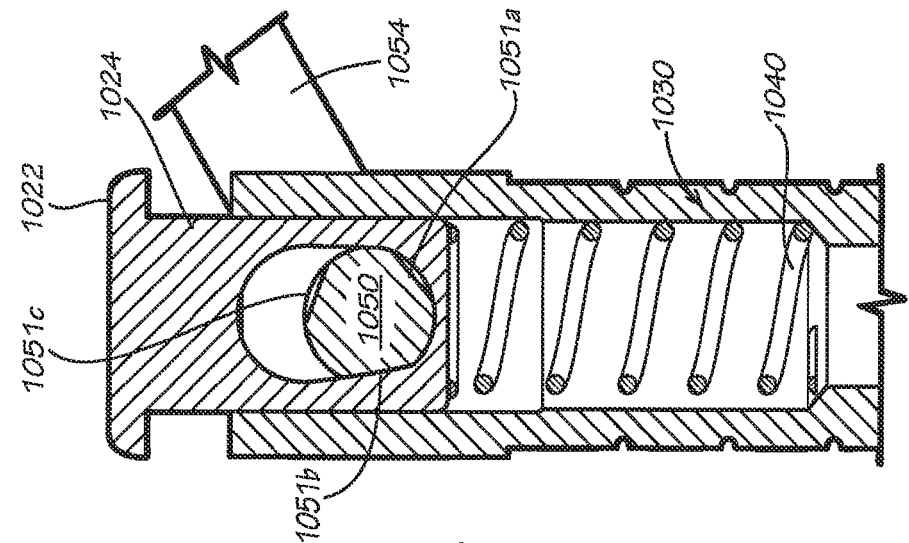
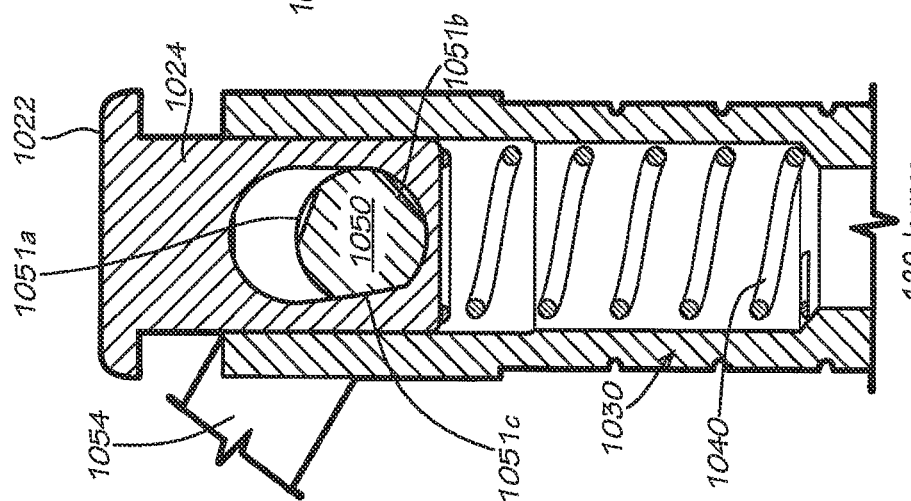
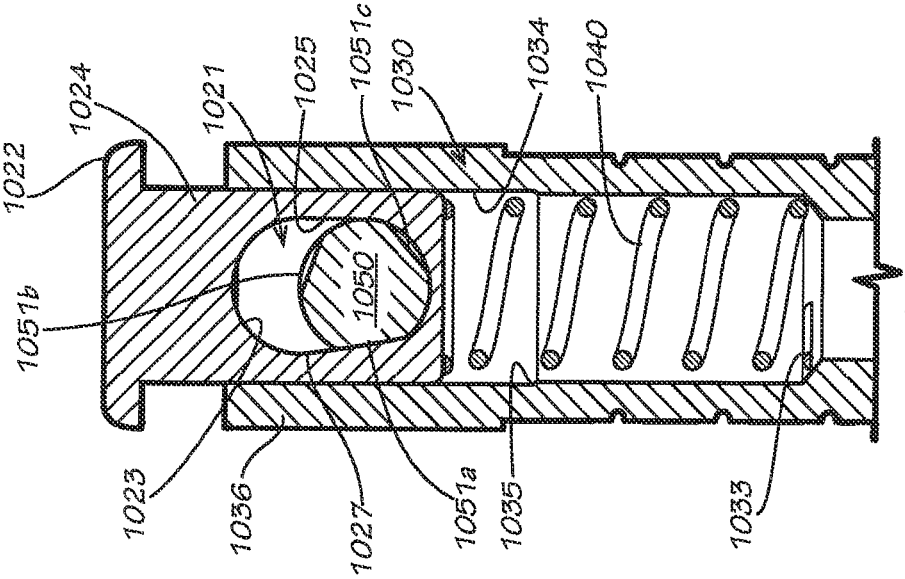

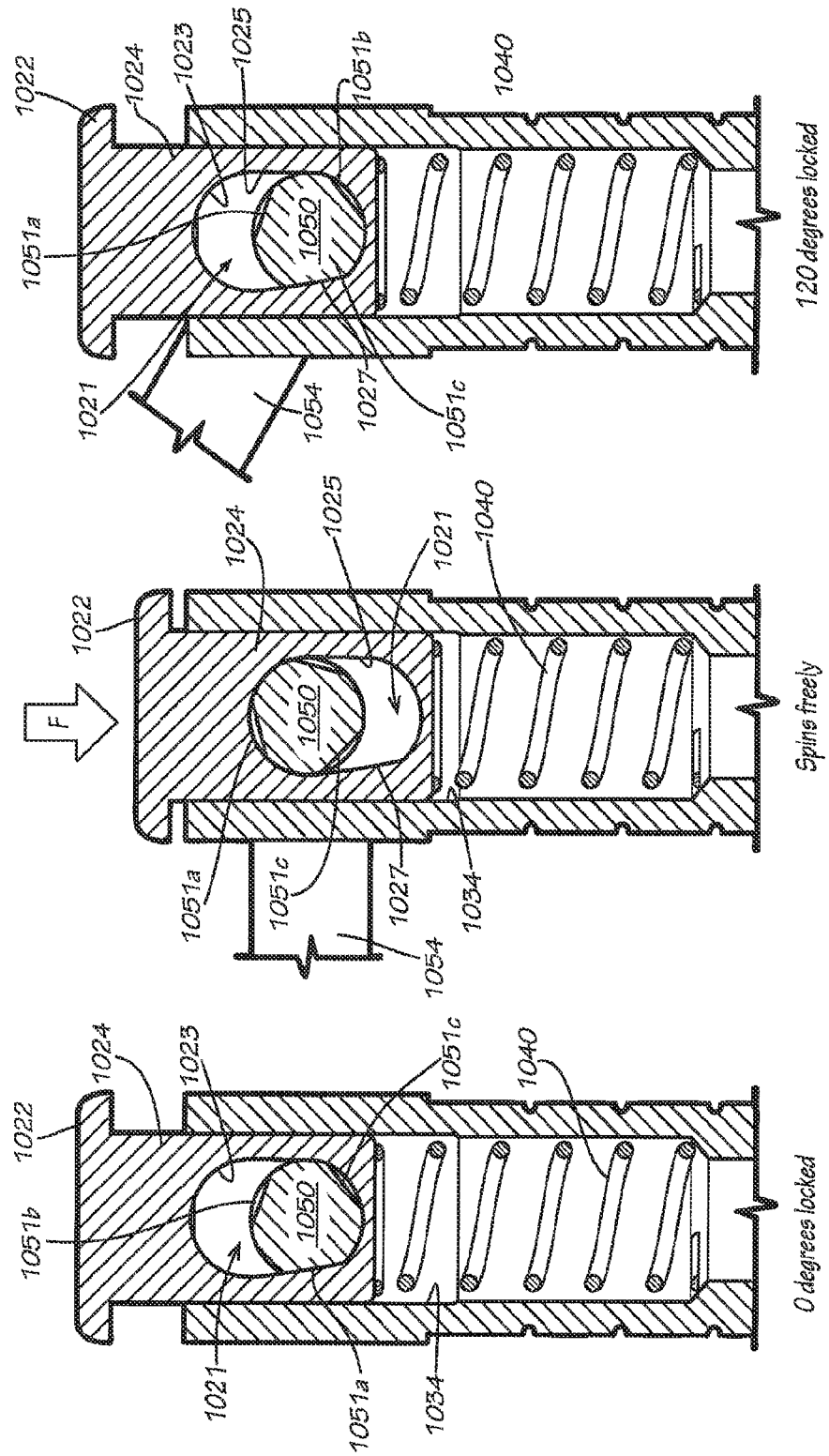

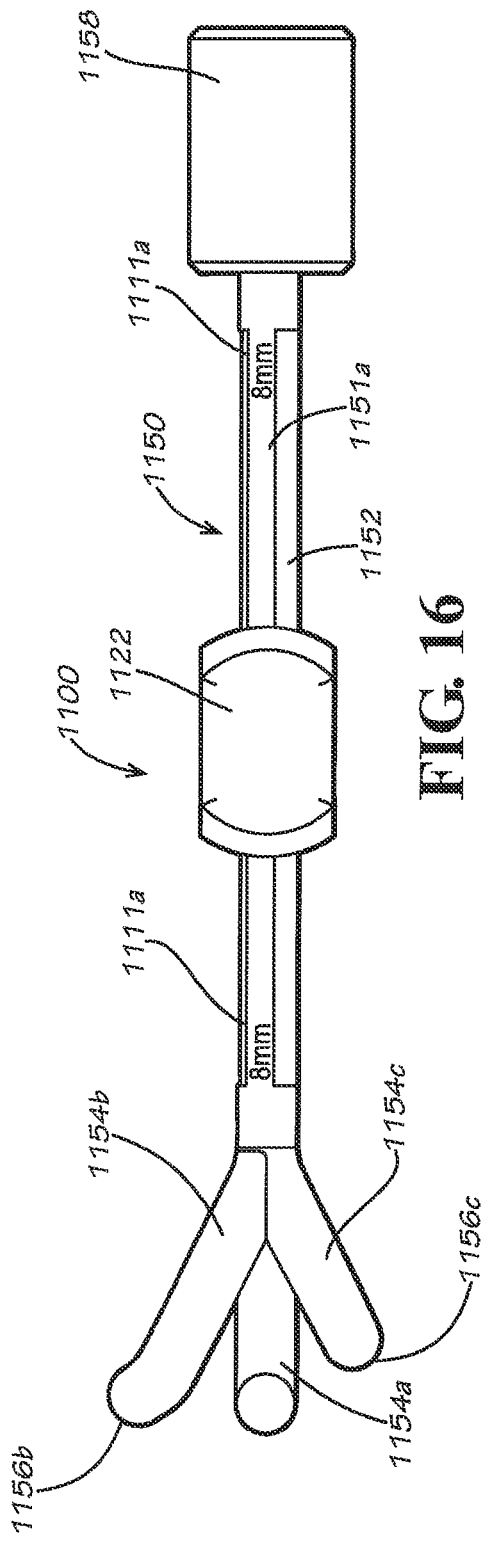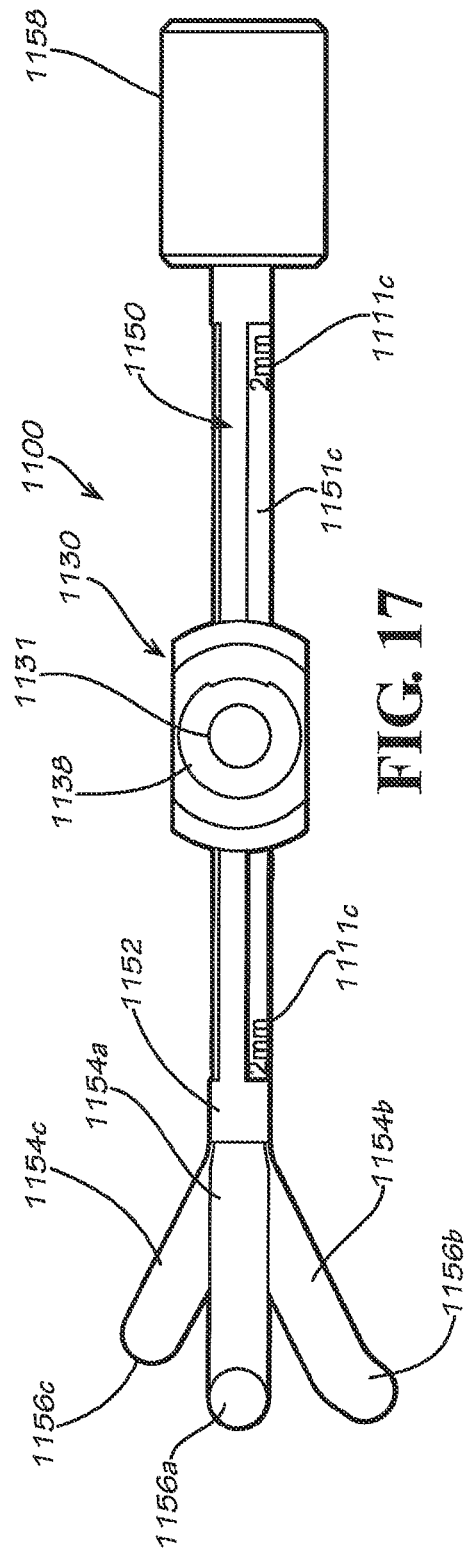

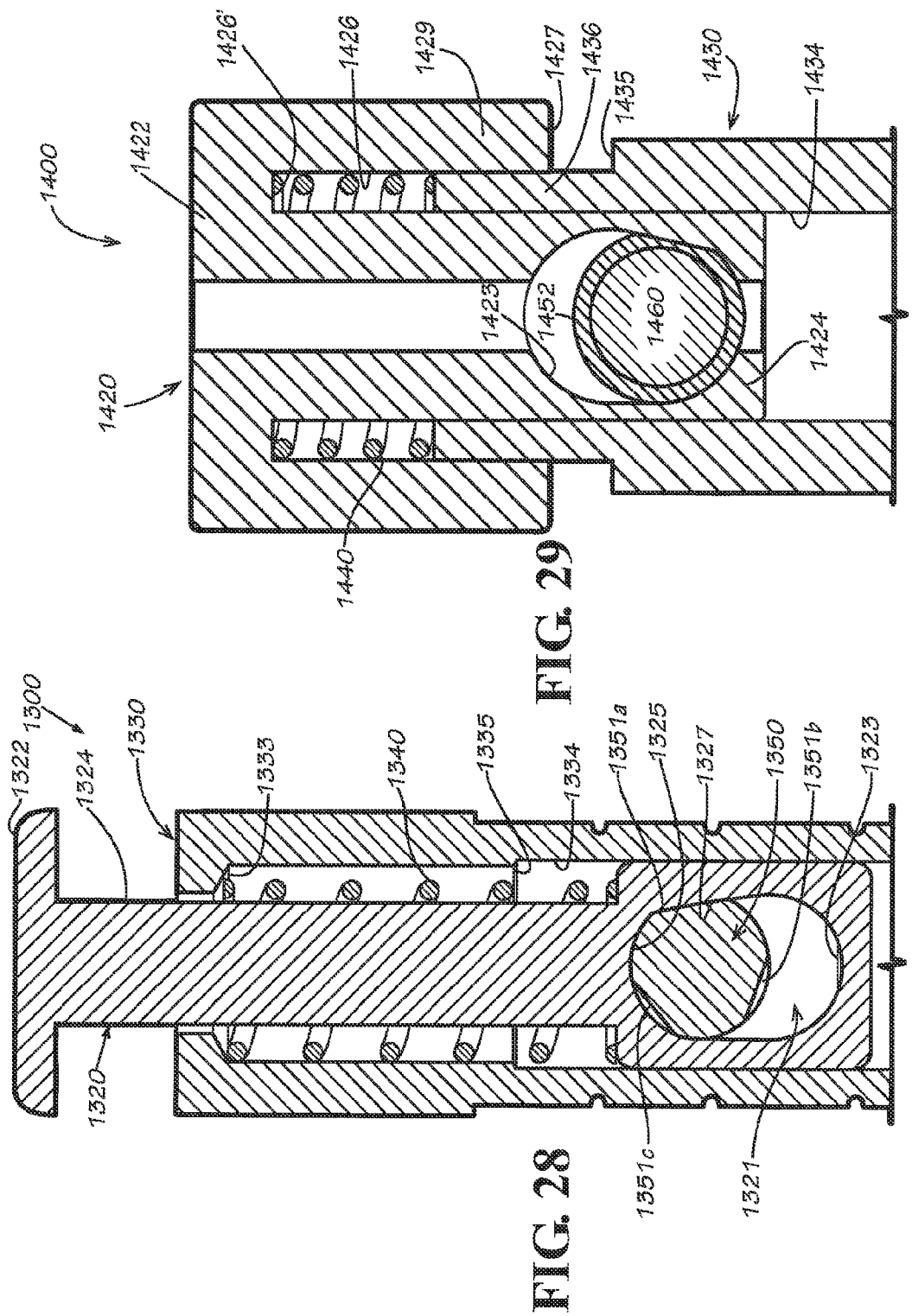

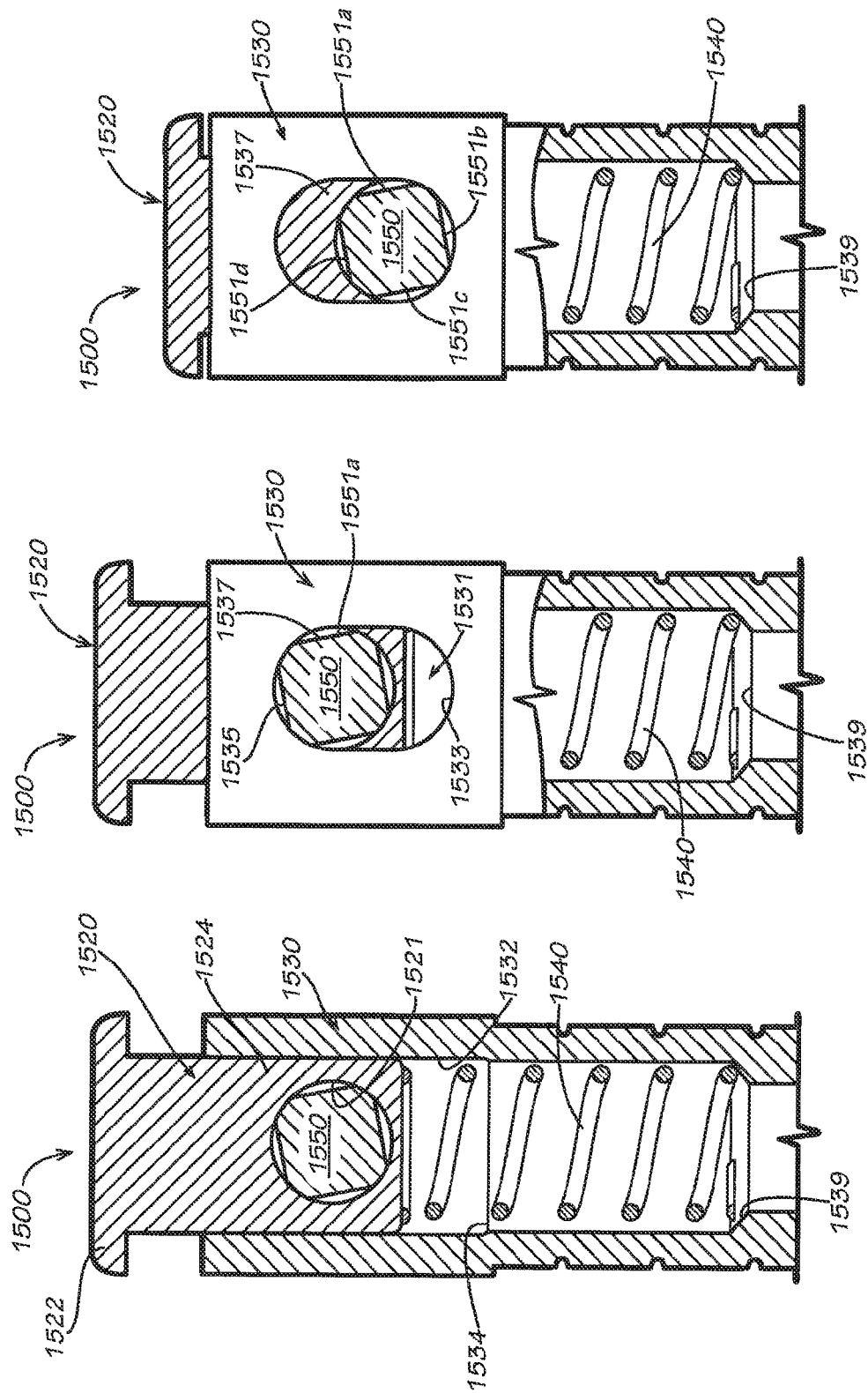

LOCKABLE ORIENTATION INSTRUMENT ASSEMBLY

CROSS-REFERENCE TO RELATED APPLICATIONS

This application is a continuation-in-part of, and claims priority to U.S. patent application Ser. No. 11/344,778 filed on Feb. 1, 2006 which published as U.S. Patent Application Publication Number US-2006/0179979 A1 on Aug. 17, 2006, and which claims the benefit of U.S. Provisional Patent Application Ser. No. 60/649,059 filed on Feb. 1, 2005, the entire contents of which are incorporated herein by reference.

FIELD OF THE INVENTION

The present invention relates generally to surgical instrumentation and more particularly to lockable instrument assemblies for quick and easy positioning of surgical instrumentation.

BACKGROUND OF THE INVENTION

Surgical procedures generally involve the preparation of an anatomical site for attachment of an implant or other prosthetic device. Such preparations generally require surgical instrumentation having various components working together to facilitate one or more surgical tasks performed by the surgeon. In many cases, redundant components are necessary to perform the same surgical function for slightly different situations. For instance, a set of like components may be provided in different sizes to accommodate anatomies of different patients. Such redundancies contribute to instrumentation complexity, size, and cost.

Previous efforts have been made to address this problem. For example, surgical instrumentation has been provided with modular components for improved versatility. However, such modularities employ crude locking mechanisms between components which can loosen during the surgical procedure.

In some surgical procedures, measuring devices are provided as part of the surgical instrumentation and are generally used to reference portions of anatomy, locate a surgical instrument with respect to an anatomical landmark, or reposition a first surgical instrument relative to another surgical instrument. Such devices are typically provided as solid, homogeneous, one-piece components configured to be displaced from another component. Such devices are also generally bulky, sit proud in relation to the surgical instruments to which they are attached, and cannot be temporarily adjusted for easy ingress and egress from small surgical sites. Therefore, conventional measuring devices can be difficult or impossible to use with minimally-invasive surgical approaches.

Locking mechanisms which are typical of the prior art utilize setscrews or levers having cam portions, and require a surgeon to constantly re-apply the necessary tightening torques to ensure that components do not loosen during anatomical referencing and other various surgical steps. Loosening of such prior locking mechanisms is common when instrumentation is used in small surgical spaces (i.e., where interference with soft tissue is likely) and in high vibration environments (e.g., when performing surgical steps such as cutting, reaming, pinning, impacting, drilling, and broaching).

Loosening of surgical instrumentation components during a surgical procedure may lead to implant malpositioning, poor implant fit, prolonged surgery time, and adverse patient outcomes. Therefore, there is a need for improved lockable instrument assemblies that allow a surgeon to quickly adjust a first instrumentation component relative to a patient's anatomy or relative to a second instrumentation component. There is also a need for improved lockable instrument assemblies that allow a surgeon to instantaneously lock or unlock first and second instrumentation components together and prevent relative movement therebetween. There is also a need for improved lockable instrument assemblies which are configured to temporarily avoid potential interferences with other surgical instrumentation and portions of anatomy (e.g., soft tissue, cartilage, and bone), particularly in minimally invasive surgical procedures. There is also a need to provide lockable instrument assemblies having improved locking strength characteristics between a first instrumentation component and a second instrumentation component, in order to prevent the first instrumentation component from becoming unintentionally or accidentally unlocked with respect to the second instrumentation component. Additionally, there is a need for improved instrument assemblies which enable surgeons to quickly lock, un-lock, and adjust instrumentation components in different configurations. Moreover, there is a need for improved instrument assemblies which provide a surgeon with tactile feedback and a positive indication that surgical instrumentation components are positively locked together. Lastly, there is a need for improved instrument assemblies which maintain consistent locking forces between components between surgical steps within the same procedure and between different surgical procedures.

SUMMARY OF THE INVENTION

The aforementioned needs are satisfied by several aspects of the present invention.

According to some aspects of the invention, there are provided improved lockable instrument assemblies which are adapted for quick manipulation and positive locking of surgical instrumentation components. In particular, lockable instrument assemblies are provided with means for securing a first instrumentation component to a second instrumentation component, wherein rotation and/or translation of the first instrumentation component relative to the second instrumentation component is prevented in a locked assembly configuration, and wherein rotation and/or translation of the first instrumentation component relative to the second instrumentation component is permitted in an un-locked assembly configuration.

According to some aspects of the invention, there is also provided a method of using lockable instrument assemblies. The method comprises the step of manipulating a spatial orientation of a first instrumentation component relative to a second instrumentation component, wherein the step of manipulating a spatial orientation of a first instrumentation component involves moving the first instrumentation component in a degree of rotation and/or a distance in translation with respect to the second instrumentation component.

Further areas of applicability of the present invention will become apparent from the detailed description provided hereinafter. It should be understood that the detailed description and specific examples, while indicating certain embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIG. 1b is an exploded perspective view of the lockable instrument assembly of FIG. 1a;

FIG. 2 is a side view of the lockable instrument assembly of FIG. 1a;

FIG. 6 is a side view of a lockable instrument assembly according to other embodiments;

FIG. 7 is a coronal cross-sectional view of the lockable instrument assembly of FIG. 6;

FIG. 8 is a bottom view of the lockable instrument assembly of FIGS. 6-7;

FIGS. 9a-9c illustrate various locked assembly configurations of the lockable instrument assembly of FIGS. 6-8;

FIGS. 10a-10c are coronal cross-sectional views of the lockable instrument assembly in each of the locked assembly configurations shown in FIGS. 9a-9c, respectively;

FIGS. 11-13 illustrate the steps of locking, unlocking, re-configuring, and re-locking the lockable instrument assembly in a different locked assembly configuration;

FIGS. 16 and 17 are top and bottom views of the lockable instrument assembly, respectively;

FIG. 28 is an alternative embodiment which uses a pulling force to unlock a lockable instrument assembly.

FIG. 29 illustrates alternative embodiment of a lockable instrument assembly wherein a mounting body is received within a displacement member.

FIGS. 30-32 illustrate the step of unlocking another alternative embodiment of a lockable instrument assembly wherein a shaped aperture is provided on a mounting body.

DETAILED DESCRIPTION OF THE EMBODIMENTS

Figure 1A:
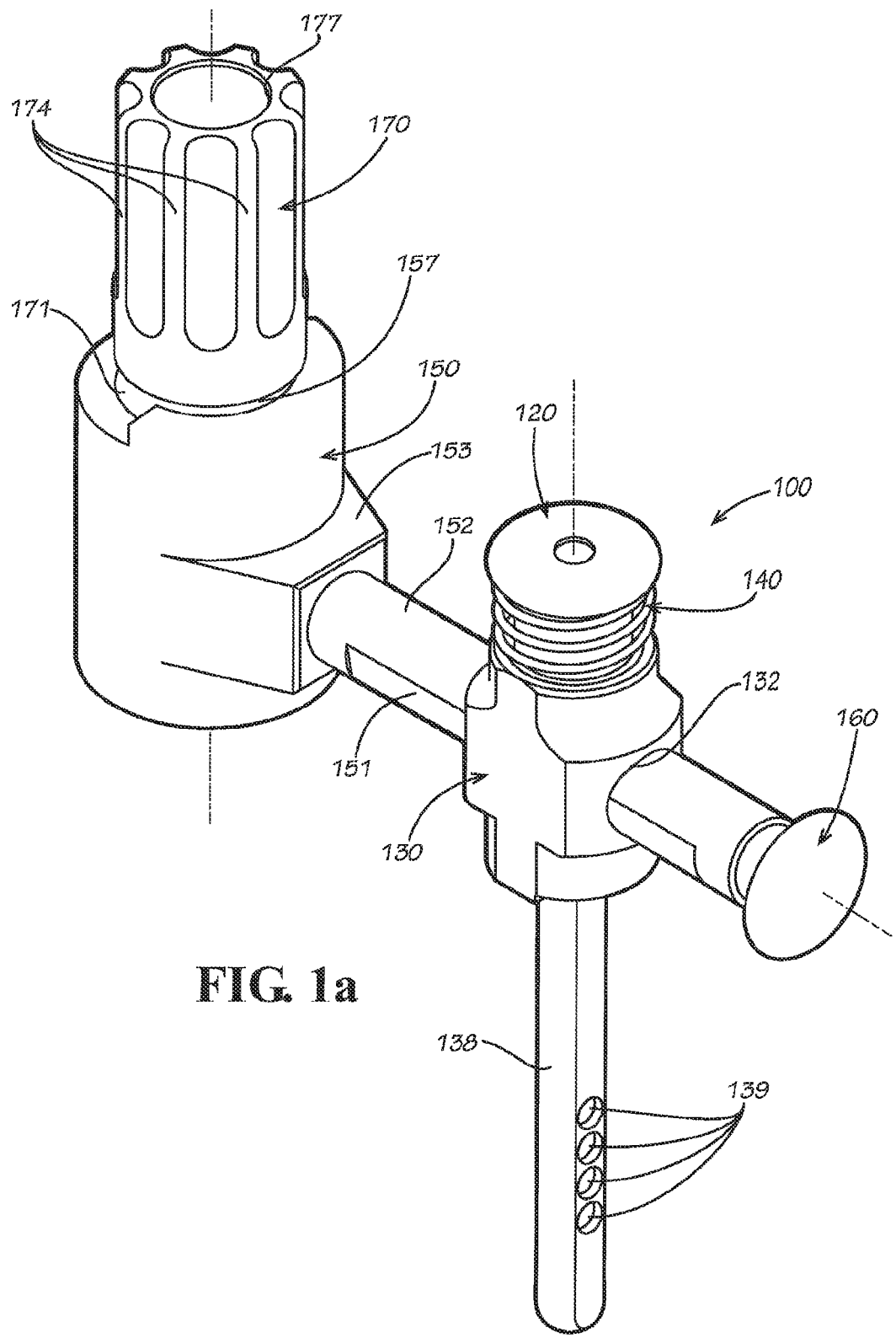
FIG. 1a is a perspective view of a lockable instrument assembly according to some embodiments.
Figure 1B:
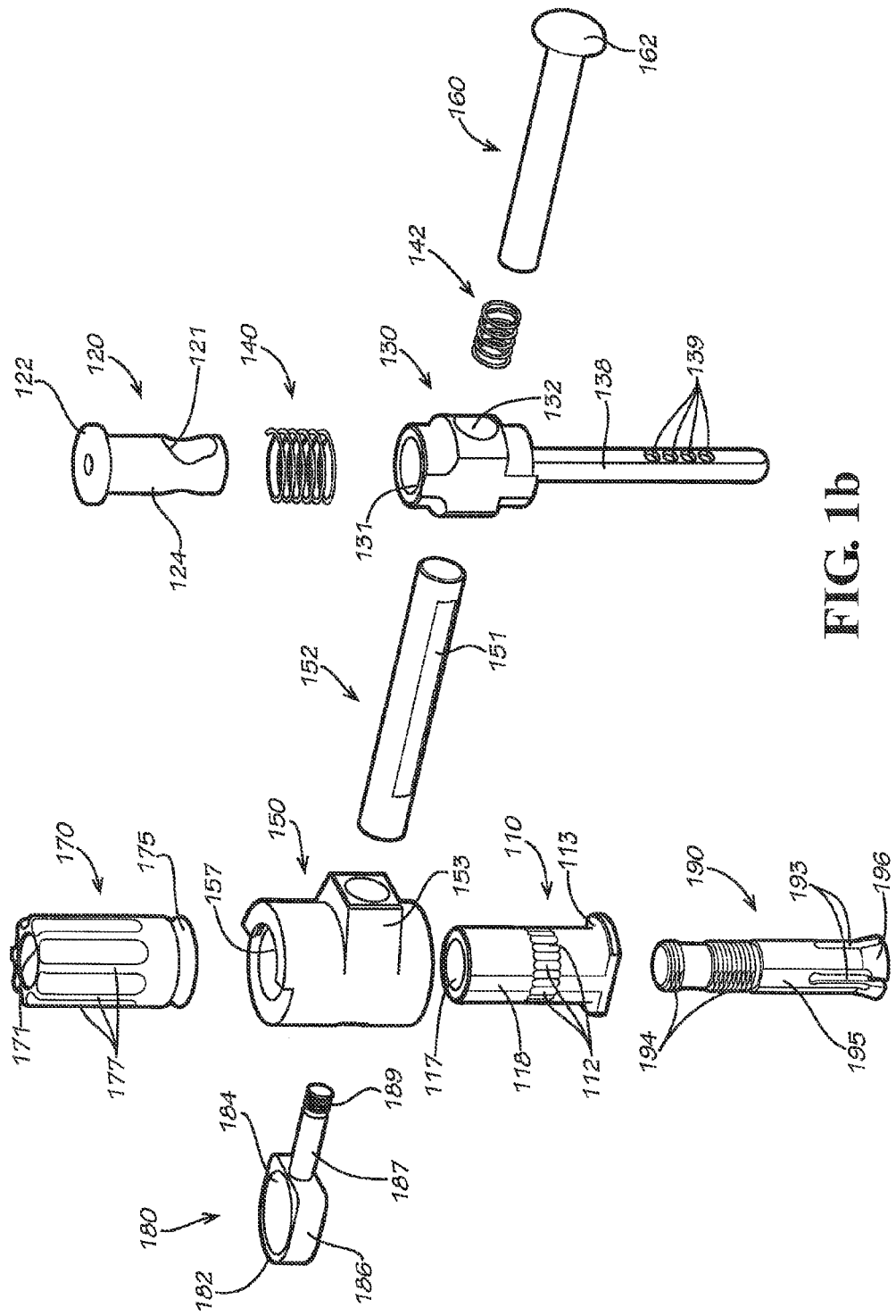
Figure 2:
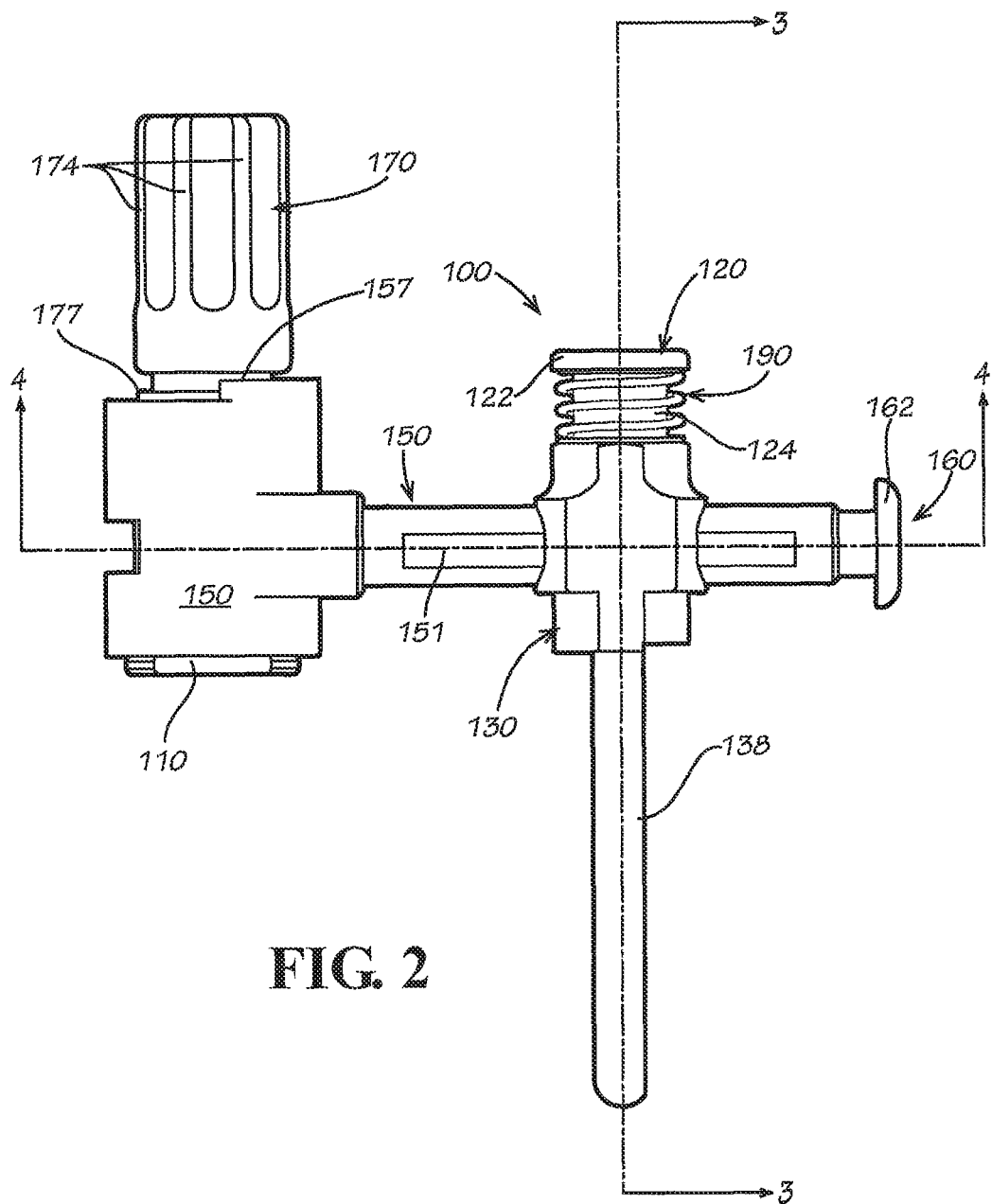
Figure 3:
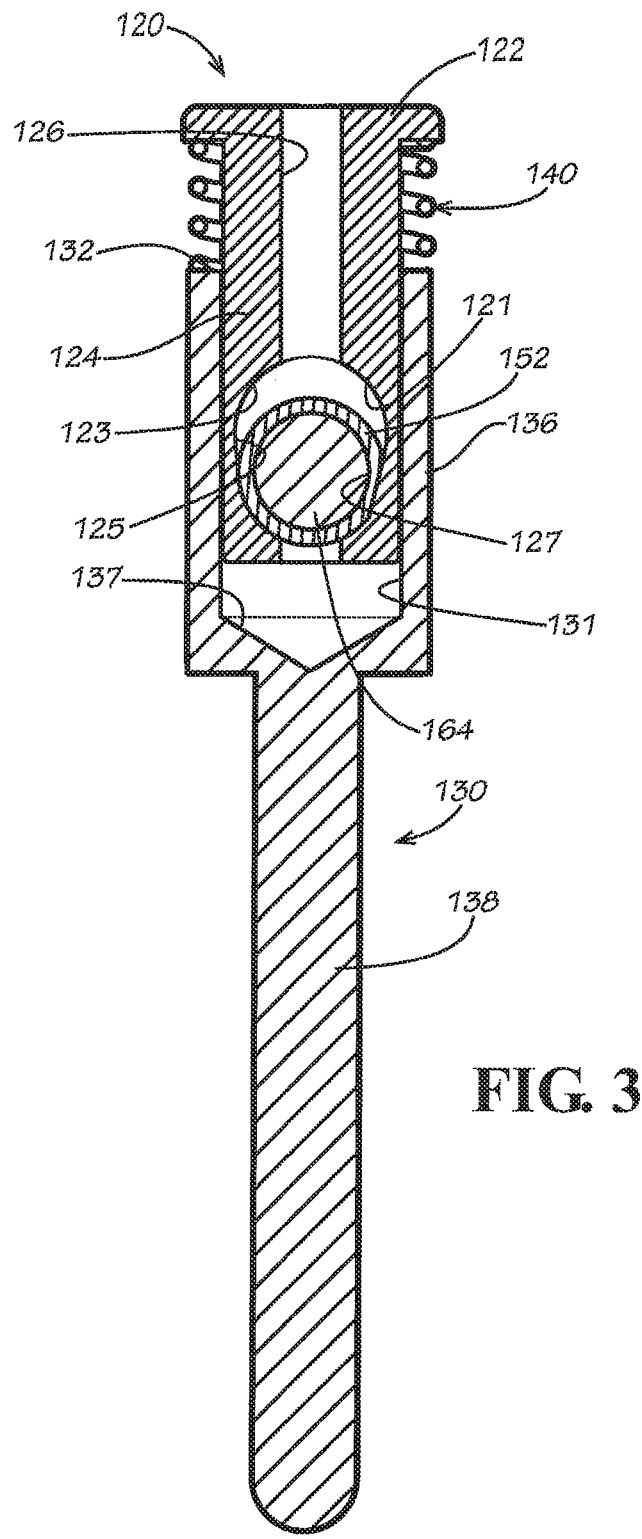
FIG. 3 is a coronal cross-sectional view of the lockable instrument assembly of FIG. 2.

The following description of the preferred embodiment(s) is merely exemplary in nature and is in no way intended to limit the invention, its application, or uses.

FIGS. 1a-5 are generally drawn to a lockable instrument assembly 100 for attaching a first instrumentation component 300 to a second surgical instrumentation component 200 according to a first embodiment. The first instrumentation component 300 may be a surgical guide as shown and the second surgical instrumentation component 200 may be an intramedullary rod. The lockable instrument assembly 100 generally comprises a mounting body 130 having a housing portion 136 and a mounting portion 138. The mounting portion 138 may generally serve as an attachment feature for attaching the first instrumentation component 300 to the mounting body 130. Alternatively, the first instrumentation component 300 may be integral with or homogeneously formed as a portion of the mounting body 130. A receiving portion 131 such as a bore or recess having a cross-sectional shape extends into the housing portion 136, and may include a stopping portion 137. One or more location features 139 may be provided to portions of the mounting body 130 which serve to identify a spatial relationship between the mounting body 130 and the first instrumentation component 300.

A displacement member 120 is also provided within the lockable instrument assembly, the displacement member 120 having a flange 122, an insertion portion 124, and a transversely-extending shaped aperture 121. The insertion portion 124 of the displacement member 120 has a cross-sectional shape which is complementary to the receiving portion 131 of the mounting body 130, such that the displacement member 120 is slidably received within the receiving portion 131. The shaped aperture 121 comprises a non-circular annular profile when viewed along its longitudinal axis and further comprises a clearance portion 123, a locking portion 125, and one or more rotation prevention features 127 which are configured to prevent rotation of an adjustment member 150 that is received in the shaped aperture 121. One or more cavities 126 may be provided within the displacement member 120 in order to reduce material and weight of the assembly 100 and improve cleanability of the assembly during sterilization processes. A first biasing member 140 is interposed between the displacement member 120 and the mounting body 130. In some embodiments, the first biasing member 140 may be located outside of the mounting body 130, wherein in other embodiments, the first biasing member 140 may be disposed within the receiving portion 131 to conceal it from the surgical environment. The stopping portion 137 may be configured to prevent over-displacement of the displacement member 120 relative to the mounting body 130, or prevent permanent deformation of the first biasing member 140. The stopping portion 137 may also be configured to align the adjustment member 150 with the clearance portion 123 of the shaped aperture 121 when the displacement member 120 is fully pressed, so that the adjustment member 150 can translate and rotate freely with respect to the displacement member 120.

The adjustment member 150 generally comprises a housing 153 having a holding member 157, and a shaft 152 having one or more rotation prevention features 151 provided on its outer surface. While the adjustment member 150 may be formed as a single unitary piece, the shaft 152 and the housing 153 may be two separate pieces which are integrally joined by pressing, welding, threading, adhering, or otherwise connecting the shaft 152 to the housing 153, in order to reduce manufacturing costs and facilitate assembly. The holding member 157, generally serves to limit or prevent the axial displacement of an internally or externally-threaded knob 170 relative to the adjustment member 150 as will be discussed hereinafter. The holding member 157 may be provided, for example, in the form of an undercut shelf, a lip, a flange, a protuberance, a recess, or a groove, so long as it is configured to maintain the threaded knob 170 in close proximity with the adjustment member 150 and allow rotation of the threaded knob 170 with respect to the adjustment member 150.

A plunger 160 having a shaft 164, an end portion 166, a receiving portion 161 provided at said end portion 166, and a flange 162 at an end opposite to said end portion 166 may be slidably received within the shaft 152. A connecting feature 163, for example a threaded section may be provided to the receiving portion 161 of the plunger 160. The connecting feature 163 is configured to engage a complementary connecting feature 189 located on an actuator 180. The plunger 160 generally serves to move the actuator 180 between locked and unlocked positions which will be discussed hereinafter. It should be understood that the actuator 180 and the plunger 160 may be formed as a single unitary piece; however, they are shown to be two separate pieces which are integrally joined via connecting features 163, 189, in order to reduce manufacturing costs and facilitate assembly. It should also be noted that connecting features 163, 189 described herein may comprise male or female features which can be reversed as a matter of preference.

Figure 4:
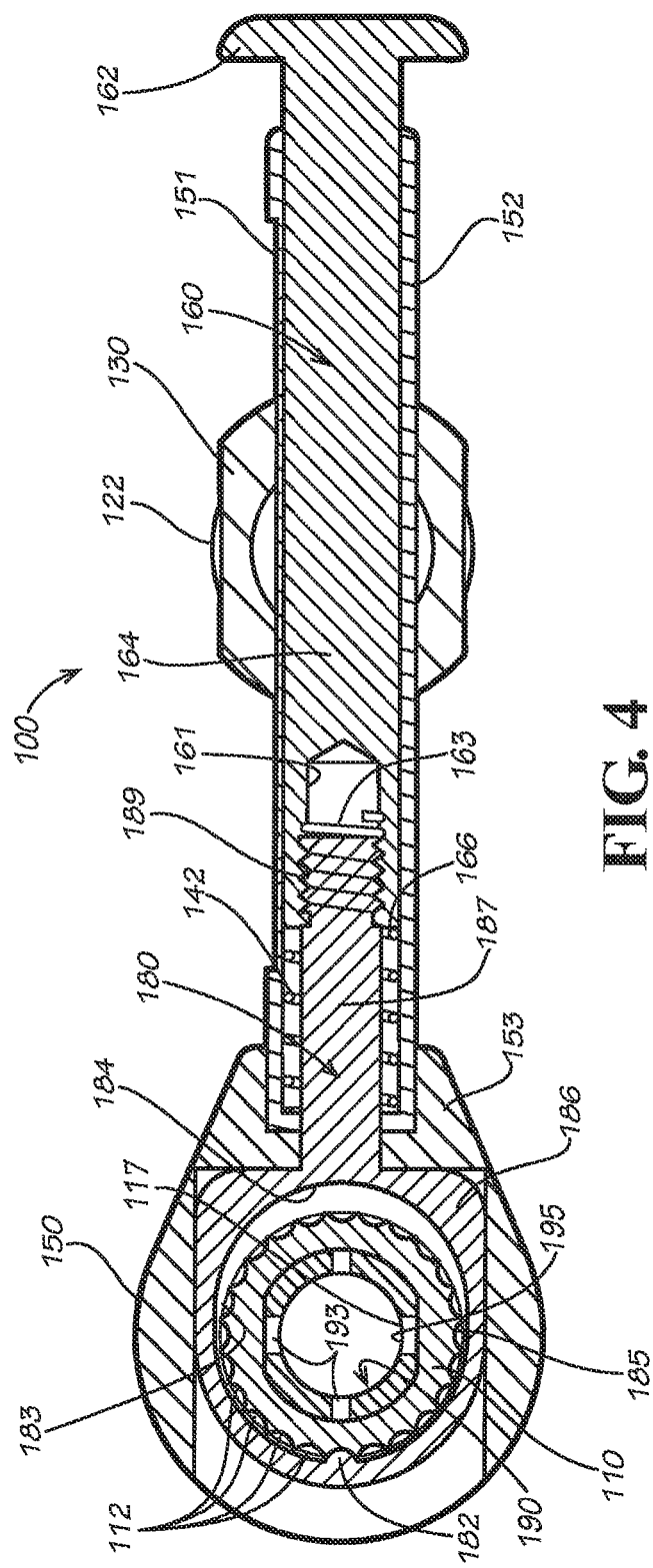
FIG. 4 is a transverse cross-sectional view of the lockable instrument assembly of FIG. 2.

Turning to FIGS. 1a and 4, adjustment member 150 forms a portion of an assembly comprising an internally or externally-threaded knob 170, a collet 190 engageable with and moveable relative to said threaded knob 170, a sleeve 110, and an actuator 180. The collet 190 may be provided with one or more slit portions 193 at a wider conical or flared end 196 in order to facilitate the expansion and contraction of the collet 190. Expansion and contraction of the collet 190 reduces and increases clamping forces around the second surgical instrumentation component 200, respectively. The collet 190 further comprises one or more internal or external threaded portions 194 which are engageable with and cooperate with the threads on the threaded knob 170. Sleeve 110 receives the collet 190, and one or more rotation prevention features 195 may be provided along outer portions of said collet 190 in order to prevent rotation of the collet 190 within the sleeve 110.

Outer portions of the sleeve 110 may comprise one or more rotation prevention features 112, 118 such as flats, notches, ridges, steps, ratchet surfaces, grooves, or cutout portions, without limitation. Some rotation prevention features 118 may prevent relative rotation between the sleeve 110 and adjustment member 150. Inner portions of the sleeve may also comprise one or more rotation prevention features 117 which prevent relative rotation between the sleeve 110 and the collet 190. Sleeve 110 may further comprise means for limiting its axial displacement 113 relative to other portions of the assembly 100, said means comprising, for example, a flange, a buttress, a shoulder, a finger, a nubbin, a step portion, or the like, in order to prevent the sleeve 110 from passing entirely through the adjustment member 150. Inner portions of the sleeve 110 adjacent to and cooperating with the wider conical or flared end 196 of the collet 190 may also be tapered, flared, or chamfered in order to provide a mechanical advantage that facilitates expansion and contraction of the collet 190 and loosens and tightens the collet 190 to the second surgical instrumentation component 200.

Sleeve 110 is provided within a shaped aperture 184 of the actuator 180, the shaped aperture 184 having a non-circular annular profile when viewed along its longitudinal axis and further comprising a locking portion 182 having one or more rotation prevention features 181, and one or more elongated aperture portions 183, 185 which extend to a clearance portion opposite of the locking portion 182. The actuator 180 shown comprises a body 186 and shaft 187 extending therefrom; however, the shaft 187 may be eliminated and replaced by a longer shaft 164 on the plunger 160. As previously mentioned, a connecting feature 189 may be provided at a free end of the shaft 187, in order to engage a complimentary connecting feature 163 on an end portion 166 of the plunger 160 and rigidly connect the two pieces together. A second biasing member 142 may be provided, for instance, between the end portion 166 of the plunger body 160 and the adjustment member 150. The second biasing member 142 generally serves to urge the actuator 180 towards the locking portion 182 of the shaped aperture 184 such that at least one rotation prevention feature 181 in the shaped aperture 184 is normally engaged with one or more rotation prevention features 112 on the sleeve 110. This locked assembly configuration prevents rotation and/or translation of at least one first instrumentation component 300 associated with the assembly 100 relative to at least one second instrumentation component 200 associated with the assembly 100. The locked assembly configuration also prevents movement of at least one first instrumentation component 300 associated with the assembly 100 relative to the patient's anatomy 400. The second instrumentation component 200, collet 190, sleeve 110, and threaded knob 170 generally remain in a fixed relationship with each other in a locked assembly configuration, the sleeve 110 generally serving as an extension of the second instrumentation component 200 and providing rotation prevention means 112. Providing the sleeve 110 with one or more rotation prevention features 112 eliminates the need to provide similar rotation prevention features directly to outer portions of the second instrumentation component 200. Therefore, sleeve 110 may also serve as an adapter for the lockable instrument assembly so that it can be used with a conventional instrumentation component 200.

When a force is applied to the plunger 160, the plunger 160 is moved relative to adjustment member 150 from a locked assembly configuration to an unlocked assembly configuration. The force temporarily overcomes a forces exerted by the second biasing member 142, and therefore the actuator 180, adjustment member 150, mounting body 130, displacement member 120, plunger 160, first and second biasing members 140, 142, and any instrumentation component 300 that may be connected to the assembly 100 are allowed to rotate and/or translate in relation to the second instrumentation component 200. When the force to the plunger 160 is removed, the second biasing member 142 returns the plunger 160 to its normal position and the lockable instrument assembly 100 returns to a locked assembly configuration. Accordingly, one or more rotation prevention features 181 located adjacent the locking portion 182 of the actuator 180 engage said one or more rotation prevention features 112 on the sleeve 110 and prevent further rotation and/or translation of the actuator 180, adjustment member 150, mounting body 130, displacement member 120, plunger 160, first and second biasing members 140, 142, and any instrumentation component 300 that may be connected to the assembly relative to the second instrumentation component 200.

As shown in the exemplary embodiment illustrated, the second instrumentation component 200 may be configured as an intramedullary rod having a proximal end portion 202, one or more torque application surfaces 204, a distal end 205, and a shaft portion 206. The second instrumentation component 200 may also comprise indicia, for example indicia relating to its size, length, or serial number. One or more cutting or stabilization features 207 such as sharp edges or ridges may also be provided to the second instrumentation component 200, as well as one or more orientation markings 208. Orientation markings 208 may, for instance, be used to indicate a position of the second instrumentation component 200 relative to a patient's anatomy 400. For example, orientation markings 208 may comprise depth markings as shown. It should be understood that while the second instrumentation component is represented as an intramedullary rod, lockable instrument assemblies 100, 1000, 1120, 1200 disclosed herein may be used in conjunction with and will demonstrate equal utility with extramedullary rods, jigs, and other fixtures such as external fixation frames, without limitation.

Figure 5:
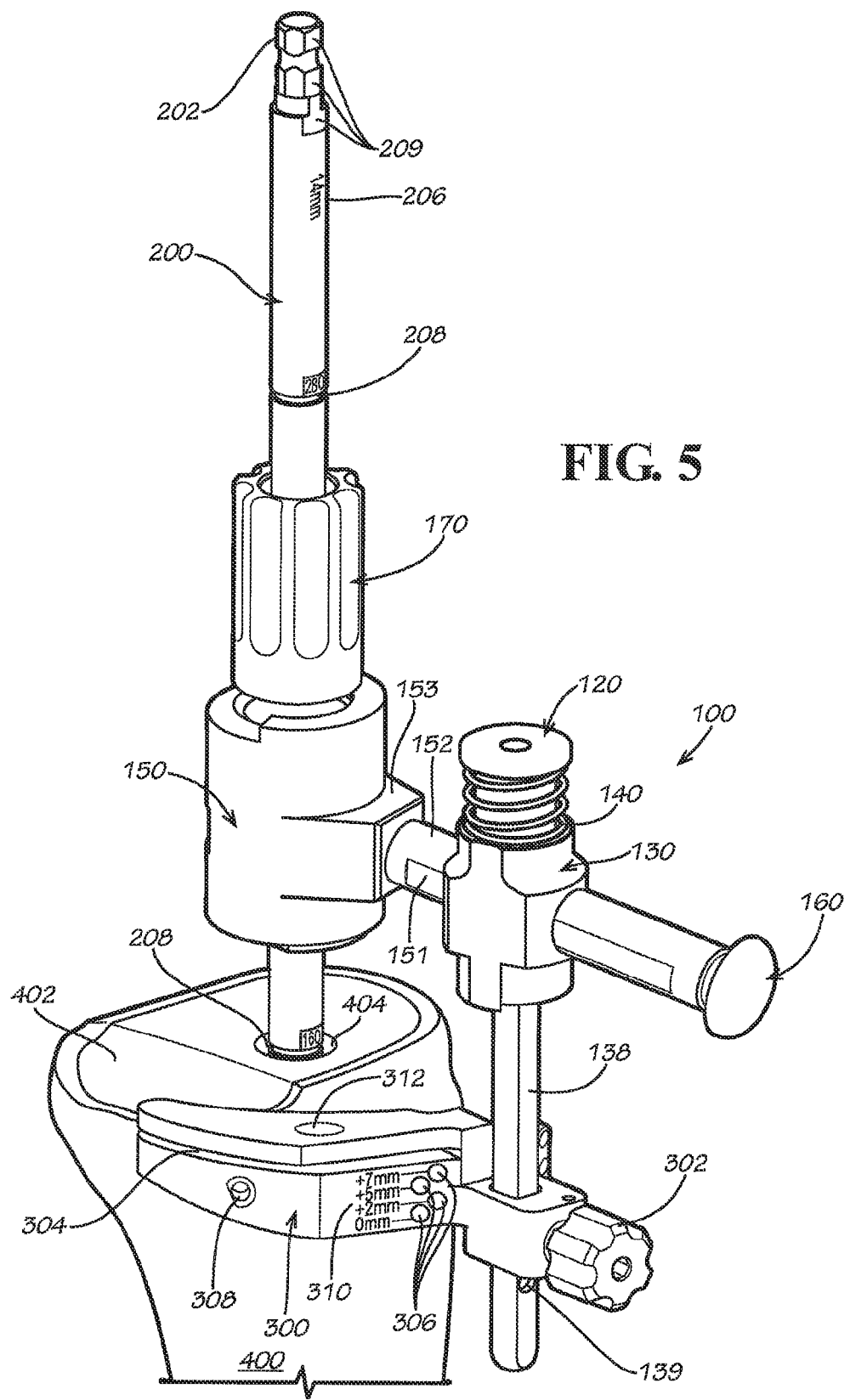
FIG. 5 is a perspective view showing one practical utility of a lockable instrument assembly.
Figures 14, 15:
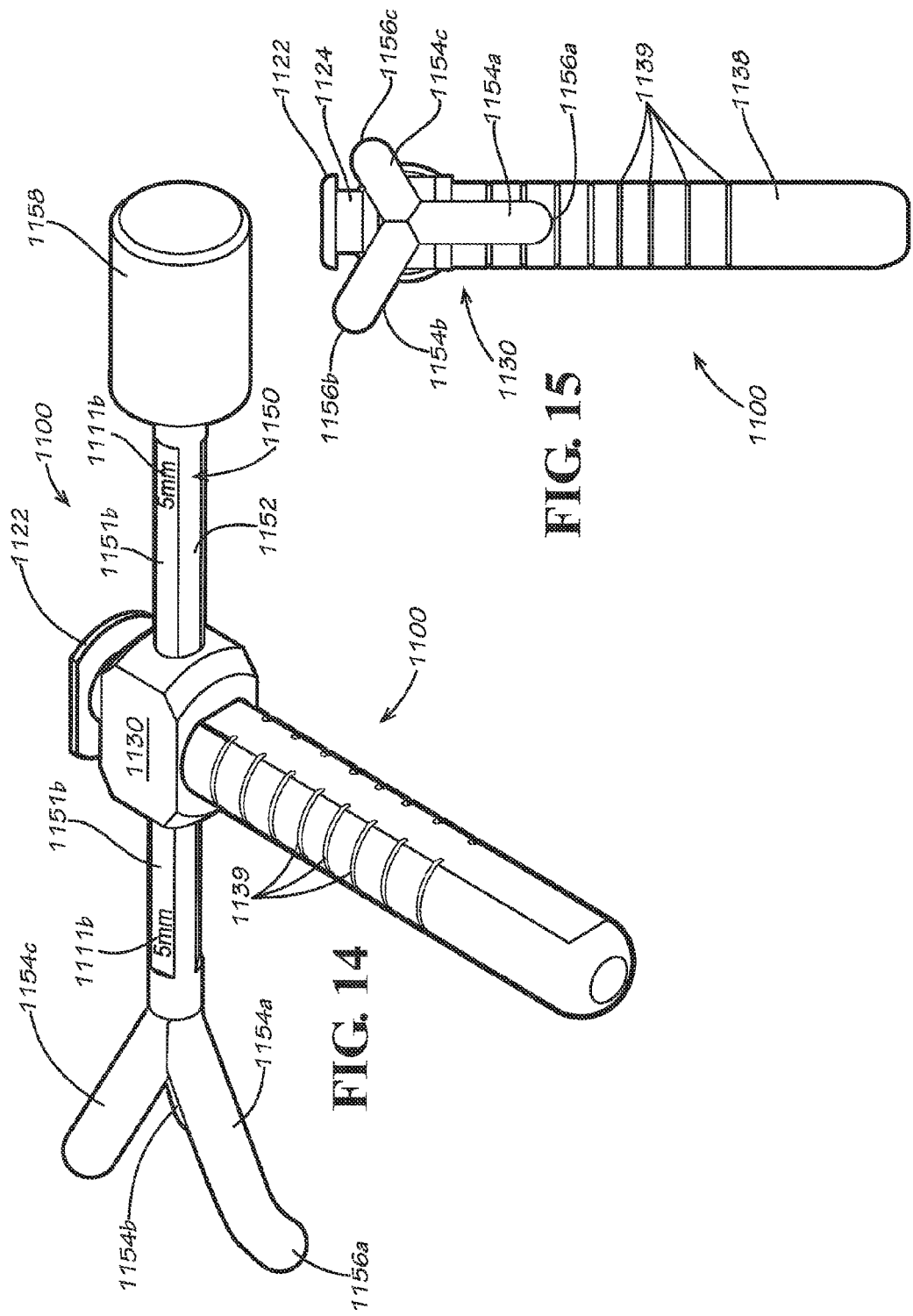
FIG. 14 is a perspective view of a lockable instrument assembly according to yet other embodiments of the invention.
FIG. 15 is a frontal view of the lockable instrument assembly of FIG. 14.
Figure 18:
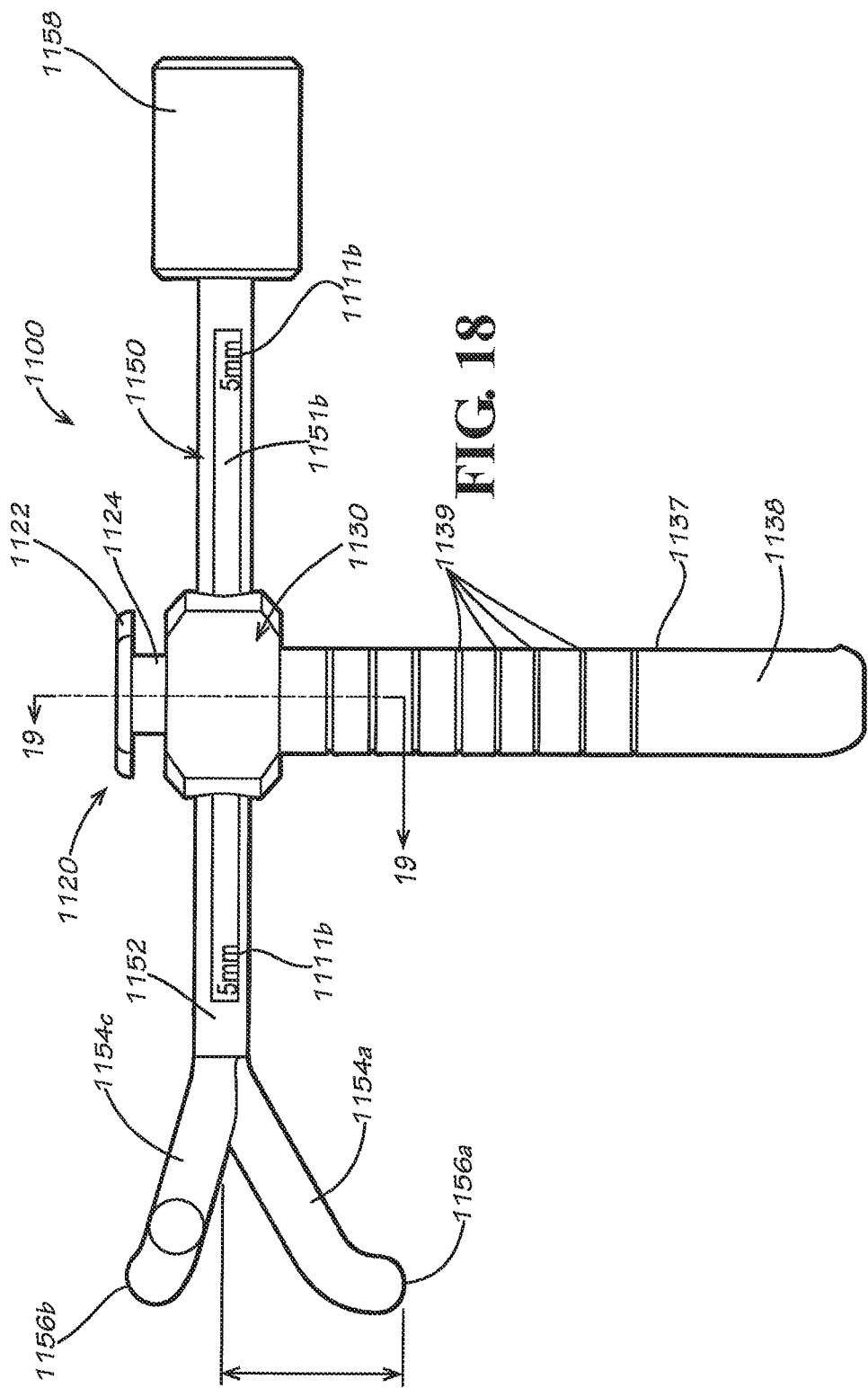
FIG. 18 is a side view of the lockable instrument assembly of FIGS. 14-17.

As shown in FIG. 5, the first instrumentation component 300 may be configured as a surgical guide for guiding a surgical tool configured to make a modification to a patient's anatomy 400. The modification may be a cut, a resection, an incision, a hole, or the like. The instrument assembly 100 is used to position and secure the surgical guide relative to the patient's anatomy 400 before or after the modification to the patient's anatomy 400 is made.

In some embodiments, the first instrumentation component 300 may include positioning indicia 310, one or more resection or cutting guide surfaces 304 such as an open or closed slots, one or more relocation feature 306 for receiving surgical fasteners (e.g., pins, guide rods, and screws), and one or more stabilization features 308 (e.g., an oblique pin hole). Securing means 302 may also be provided in order to secure the first instrumentation component 300 to the lockable instrument assembly 100. Securing means 302 can be any securing means appreciated in the art, including, but not limited to a ball plunger, a locking cam lever, a setscrew, or a threaded knob as shown. If desired, securing means 302 may also comprise a lockable instrument assembly as described herein, including a biased displacement member having a transversely-extending shaped aperture which receives the mounting portion 138. In the particular embodiment shown in FIG. 5, securing means 302 is generally configured to contact, register with, and secure to one or more of the location features 139 on the mounting body 130. It should be understood that while the first instrumentation component 300 is shown to include resection or cutting guide surfaces 304 configured for use with an oscillating or reciprocating-type saw blade, the surfaces 304 may comprise geometries which are configured to guide other surgical tools such as milling devices, burring devices, rotary tools, reciprocating tools, drilling tools, and cautery devices, without limitation.

FIGS. 6-13 are drawn to a lockable instrument assembly 1000 according to another embodiment. The lockable instrument assembly 1000 is configured to lock a first instrumentation component 1050 in multiple positions relative to a second instrumentation component 1030, and allow both rotational and translational movement between the first 1050 and second 1030 components when the assembly 1000 is in an unlocked assembly configuration. In the exemplary embodiment shown, the lockable instrument assembly 1000 is provided as a measuring instrument, such as a stylus. Multiple locked assembly configurations allow portions 1054 of an adjustment member 1050 to be temporarily moved away from a surgical site or a portion of a patient's anatomy 400 and facilitate the insertion and extraction of the adjustment member 1050 into and from small surgical sites common with minimally-invasive procedures. Multiple locked assembly configurations also provide clearance for other instrumentation components and surgical tools used during the procedure. While the instrument assembly 1000 shows a representative embodiment where adjustment member 1050 comprises an arm portion typical of styli known in the art, the dotted circle portions shown in FIGS. 9a-c may represent portions of other surgical instrumentation components including portions of intramedullary rods, extramedullary rods, reamers, reaming devices, surgical impactors, impacting devices, impaction grafting devices, cutting blocks, cutting jigs, cutting tools, alignment guides (e.g., varus/valgus, flexion/extension, internal/external rotation, anterior-posterior, superior-inferior, and medial-lateral), broaching devices, milling devices, external fixation frames, pin or guidewire locating guides, targeting devices, referencing tools for use with computer-assisted surgical (CAS) navigation systems, and combinations thereof, without limitation.

Turning now to FIGS. 6-8, a lockable instrument assembly 1000 comprises a mounting body 1030 having a housing portion 1036, a mounting portion 1038, at least one receiving portion 1031, 1032, 1034 extending within said mounting body 1030, one or more stopping portions 1033, 1035 which may be formed by dimensional changes between said receiving portions 1031, 1032, 1034, one or more mounting surfaces 1037, and one or more location features 1039. In some embodiments, the at least one receiving portion 1031, 1032, 1034 may be provided as a bore, as shown, and may have any suitable cross-sectional shape. Alternatively, the at least one receiving portion 1031, 1032, 1034 may comprise one of two portions of a dovetail joint or a track as will be discussed hereinafter.

As shown in FIGS. 10a-13, a displacement member 1020 is received by the at least one receiving portion 1031, 1032, 1034. The displacement member 1020 may comprise a flange 1022 and an insertion portion 1024 depending from the flange 1022. The insertion portion 1024 is configured to communicate with the at least one receiving portion 1031, 1032, 1034 such that the displacement member 1020 slides freely relative to the mounting body 1030. While the shown embodiment depicts the insertion portion 1024 as a generally smooth cylindrical body that slides within a smooth cylindrical receiving portion 1034, it should be noted that other suitable insertion portion cross-sections may be used, so long as they are operable with the at least one receiving portion 1031, 1032, 1034. For instance, while not shown, the insertion portion 1024 may include one portion of a dovetail joint or track which communicates with a complementary mating portion of said dovetail joint of the at least one receiving portion 1031, 1032, 1034. One of ordinary skill in the art will also appreciate that the at least one receiving portion 1031, 1032, 1034 and the insertion portion 1024 may be of the male or female type, and may be reversed without consequence.

The flange 1022 generally serves to provide a gripping structure to the displacement member 1020, but it may also serve as a stopping portion to limit movement between the mounting body 1030 and displacement member 1020. Flange 1022 may further serve as a push button or pull handle to easily allow a surgeon to move the displacement member 1020 relative to the mounting body 1030. A transversely-extending shaped aperture 1021 extends through the displacement member 1020, the shaped aperture 1021 comprising a clearance portion 1023 and a locking portion 1025 having one or more rotation prevention features 1027, for instance, flat or straight portions as shown. The shaft 1052 of an adjustment member 1050 is received within said shaped aperture 1021 such that the adjustment member 1050 can be rotated freely and moved along an axis in translation within the aperture 1021 when the adjustment member 1050 is positioned in close proximity to the clearance portion 1023. However, the adjustment member 1050 is prevented from rotating and moving in translation within the shaped aperture 1021 when it is positioned in close proximity to the locking portion 1025 of the shaped aperture 1021. Rotational movement and translational movement of the adjustment member 1050 relative to both the mounting body 1030 and displacement member 1020 is prevented when one or more rotation prevention features 1051a-c located on the adjustment member 1050 engage one or more complementary rotation prevention features 1027 provided within the shaped aperture 1021. A gripping structure 1058 such as a knob or handle may be provided to the adjustment member 1050 in order to facilitate rotation and transverse movement of the adjustment member 1050.

Numerous surgical items may be provided on the adjustment member 1050. For example, the adjustment member 1050 may comprise a measuring arm 1054 having a surveying tip 1056. A biasing member 1040 operably provided between the displacement member 1020 and the mounting body 1030 urges the adjustment member 1050 into a normally locked position within the shaped aperture 1021 of the displacement member 1020. While the embodiment shown suggests an instance where displacement member 1020 is "pushed" against a biasing member 1040 (loaded in compression) to unlock the assembly 1000 and move adjustment member 1050, it should be noted that the orientation of the shaped aperture 1021, the geometries of assembly components, the type of biasing member 1040, and the relative connections between the biasing member 1040 mounting body 1030 and displacement member 1020 may obviously be changed, such that the displacement member 1020 can be "pulled" against the biasing member 1040 (loaded in tension) to unlock the assembly 1000 and move the adjustment member 1050. For instance, for the embodiment shown, the displacement member 1020 may be extended to pass through receiving portions 1032, 1031 of the mounting body 1030, so that the displacement member 1020 can be engaged and pulled from a second flange located on the displacement member 1020 at an opposite end of flange 1022.

FIGS. 9a-9c illustrate various locked assembly configurations which are possible with an adjustment member 1050 having multiple rotation prevention features 1051a-c thereon. In the particular embodiment shown, three rotation prevention features 1051a-c are spaced evenly around the shaft 1052, approximately 120 degrees apart. It is anticipated by the inventors, however, that any number of rotation prevention features 1051a-c may be provided to the adjustment member 1050, and that the rotation prevention features 1051a-c may be spaced in any fashion, including asymmetrically or unevenly around outer portions of the shaft 1052. In use, a force F is applied to the displacement member 1020 to urge the shaft 1052 of the adjustment member 1050 into the clearance portion 1023 of shaped aperture 1021. The adjustment member 1050 may then be rotated to one of a plurality of angles by applying a moment M to the adjustment member 1050, for instance, using gripping structure 1058. In the unlocked position, the adjustment member 1050 may also be translated a distance in a direction along the longitudinal axis of shaped aperture 1021. When the force F is removed, the biasing member 1040 returns the displacement member 1020 to the locking portion 1025 of the shaped aperture 1021 where the one or more rotation prevention features 1051a-c of the adjustment member 1050 engage the one or more rotation prevention features 1027 provided within the shaped aperture 1021. This locked assembly configuration prevents the adjustment member 1050 from movement in rotation and/or translation relative to mounting body 1030, displacement member 1020, and other surgical instrumentation.

In use, a surgeon may unlock the lockable instrument assembly 1000, rotate the adjustment member 1050 to lower an insertion profile of measuring arm 1054 to fit within a small surgical opening, and then move the adjustment member 1050 in translation such that it translates along its longitudinal axis and enters the small surgical opening. Once the adjustment member 1050 is located within the small surgical opening, it can be rotated to raise an insertion profile of measuring arm 1054 and the assembly 1000 returned to a locked assembly configuration. The ability to rotate and translate the adjustment member 1050 in an unlocked assembly configuration allows the adjustment member 1050 to avoid soft tissue, bone, cartilage, and other anatomical structures of the patient during insertion into a small surgical site.

FIGS. 10a-10c show three locked assembly configurations where the adjustment member 1050 is positioned and locked at zero, one-hundred twenty, and two-hundred forty degrees of rotation, respectively, in relation to mounting body 1030 and displacement member 1020. In some instances, such locked assembly configurations are helpful to temporarily move a distal surveying tip 1056 away from the surgical site or portions of a patient's anatomy 400, and thereby provide clearance and better visibility during subsequent surgical steps (e.g., resection, cutting, drilling, reaming, broaching, punching, or the like). Movement of the adjustment member 1050 away from the surgical site and portions of a patient's anatomy 400 may also prevent transmission of vibration through the assembly 1000 during said subsequent surgical steps.

FIGS. 11-13 illustrate steps of engaging and disengaging an adjustment member 1050 between locked and unlocked assembly configurations according to some embodiments. As shown in FIG. 11, adjustment member 1050 is initially prevented from rotation and/or translation since biasing member 1040 urges at least one 1051a of said one or more rotation prevention features 1051a-c against one or more rotation prevention features 1027 in the shaped aperture 1021. As shown in FIG. 12, a surgeon may unlock the assembly 1000 by applying a force to the displacement member 1020. The force overcomes the locking forces exerted by the biasing member 1040 and moves a cross-section of the adjustment member 1050 into a clearance portion 1023 of the shaped aperture 1021. In this unlocked assembly configuration, the adjustment member 1050 may spin freely about its rotational axis and move in translation along said axis within the shaped aperture 1021 of the displacement member 1020. As shown in FIG. 13, when the force is removed, the biasing member 1040 urges the shaft 1052 of the adjustment member 1050 back into the locking portion 1025 of the shaped aperture 1021, such that another 1051c of said one or more rotation prevention features 1051a-c on the adjustment member 1050 rests against and frictionally engages the one or more rotation prevention features 1027 in the shaped aperture 1021. Therefore, the lockable instrument assembly 1000 is adapted to provide at least one locked and unlocked assembly configuration, wherein fine rotational and translational adjustments to the orientation of the adjustment member 1050 may be made while the assembly 1000 in said unlocked assembly configuration. The desired number of locked assembly configurations may be determined in whole or in part by the number of rotation prevention features 1027, 1051a-c, as well as their operable lengths.

FIGS. 14-19 are drawn to a lockable instrument assembly 1100 according to other embodiments. As with previous embodiments, the lockable instrument assembly 1100 is configured to lock a first instrumentation component 1150 in multiple positions relative to a second instrumentation component 1030 and allow both rotational and translational movement of the first instrumentation component 1150 relative to the second instrumentation component 1130 when the assembly 1100 is in an unlocked assembly configuration. The assembly 1100 enables a first measuring arm 1154a of an adjustment member 1150 having a first geometry and first distal surveying tip 1156a to be quickly selected from a plurality of measuring arms 1154a-c, each having different geometries. In the exemplary embodiment shown, adjustment member 1050 forms a portion of a measuring instrument, wherein each of the plurality of measuring arms 1154a-c radially extend from the shaft 1152 of the adjustment member 1050 to respective distal surveying tips 1156a-c by varying amounts of distance D. This is most clearly shown in FIGS. 15 and 18. Each distance D may correspond to a different surgical measurement from an anatomical landmark or surgical site location 402. For example, a surgeon may select a first measuring arm 1154a to position the assembly 1100 and a first instrumentation component 300 attached thereto, a specified first distance from an articular surface, or the surgeon may select a second measuring arm 1154b to position the assembly 1100 and a first instrumentation component 300 attached thereto, a specified second distance from said articular surface.

This function is particularly useful when locating anatomical modifications to be made during the procedure, for example, bone resections. In use, a surgeon may select a first measuring arm (e.g., 1154a) which corresponds to a desired first resection depth relative to an anatomical landmark or surgical site location 402, and then lock the assembly 1100 in a first locked assembly configuration corresponding to the first measuring arm 1154a. The surgeon may then attach the assembly 1100 to an instrumentation component 300 such as a cutting guide 300, via a receiving portion 312. In some instances, receiving portion 312 may be a recess, a cavity, or an aperture as shown. Attachment may be made by inserting the assembly 1100 into an aperture located on the component 300 until the distal surveying tip 1156a of the first measuring arm 1154a touches the anatomical landmark or surgical site location 402 which is being used to reference the depth of the first resection. Using indicia 1139 provided on the assembly 1100, the position of the instrumentation component 300 is adjusted relative to the assembly 1100 so that it corresponds to the first desired resection depth. Once the component 300 is properly aligned with indicia 1139, it may be secured to a portion of the patient's anatomy 400 using fixation means known in the art (e.g., pins or screws). The instrumentation component 300 may also be stabilized by securing the component 300 to other surgical instrumentation via securing means 302. In some instances, pins may be placed through at least one relocation feature 306 and into a portion of the patient's anatomy 400 in order to temporarily stabilize the component 300 in four degrees of freedom with respect to the patient's anatomy 400. Pins may additionally be placed through one or more stabilization features 308 provided on the component 300 and into a portion of the patient's anatomy 400 in order to stabilize the component 300 in all six degrees of freedom with respect to the patient's anatomy 400. The assembly 1100 may then be removed from the component 300, and an anatomical modification may be made using the component 300 to guide an anatomical modification tool (e.g., a drill, reaming device, saw, blade, milling device, osteotome, cautery, or scalpel).

If corrective modifications such as one or more second resections are necessary, the surgeon may re-configure the assembly 1100 in another locked assembly configuration by engaging and applying a force to displacement member 1120, rotating the adjustment member 1150 while said member 1150 is located in the clearance portion 1123 of the shaped aperture 1121 to index and select a second measuring arm 1154b which corresponds to a different second resection depth relative to the previously made first resection, and then releasing the displacement member 1120 to lock the assembly 1100 in a second locked assembly configuration corresponding to the second measuring arm 1154b. The surgeon may then position the assembly 1100 within the component 300 until the distal surveying tip 1156b of the second measuring arm 1154b touches a portion of the previously made first resection. Using indicia 1139 provided on the assembly 1100, the position of the component 300 relative to the assembly 1100 may be adjusted to correspond to the desired second resection depth. Once the component 300 is properly aligned with the indicia 1139, it may be re-secured to the anatomical portion 400 using one or more pins through the at least one relocation feature 306, or re-secured to the assembly 1100 in a different orientation using securing means 302. The assembly 1100 may then be removed from the component 300, and a second anatomical modification may be made using the component 300 to guide a bone modification tool (e.g., a drill, reaming device, or a saw).

Alternatively, if corrective anatomical modifications such as a second bone resection are necessary after a first anatomical modification has already been made, the instrumentation component 300 may be removed and repositioned over a previously placed pin, such that the pin is in a different relocation feature 306. Indicia 310 located on the component 300 may help indicate the location of the second anatomical modification to be made.

While FIGS. 14-19 suggest an embodiment where adjustment member 1150 comprises a measuring instrument, the basic functional mechanisms described may be advantageously applied to other surgical instrumentation components including, but not limited to: intramedullary rods, extramedullary rods, reamers and reaming devices, surgical impactors and impacting devices, mounting apparatuses, cutting blocks, cutting jigs, cutting tools, alignment guides (e.g., varus/valgus, flexion/extension, internal/external rotation, anterior-posterior, superior-inferior, and medial-lateral), broaching devices, milling devices, external fixation frames, pin locator guides, targeting devices, referencing tools for use with computer-assisted surgical (CAS) navigation systems, and combinations thereof.

Turning now to FIGS. 14-19, a lockable instrument assembly 1100 comprises a mounting body 1130 having a housing portion 1136, a mounting portion 1138, at least one receiving portion 1131, 1132, 1134 extending within said mounting body 1130, one or more stopping portions 1133, 1135 which may be formed as shelves, steps, or other dimensional changes between said receiving portions 1131, 1132, 1132, one or more mounting surfaces 1137, and one or more location features 1139. In some embodiments, the at least one receiving portion 1131, 1132, 1134 may be provided as a bore, as shown, and may have any suitable cross-sectional shape. Alternatively, the at least one receiving portion 1131, 1132, 1134 may comprise one of two portions of a dovetail joint or a track as will be discussed hereinafter.

Figure 19:
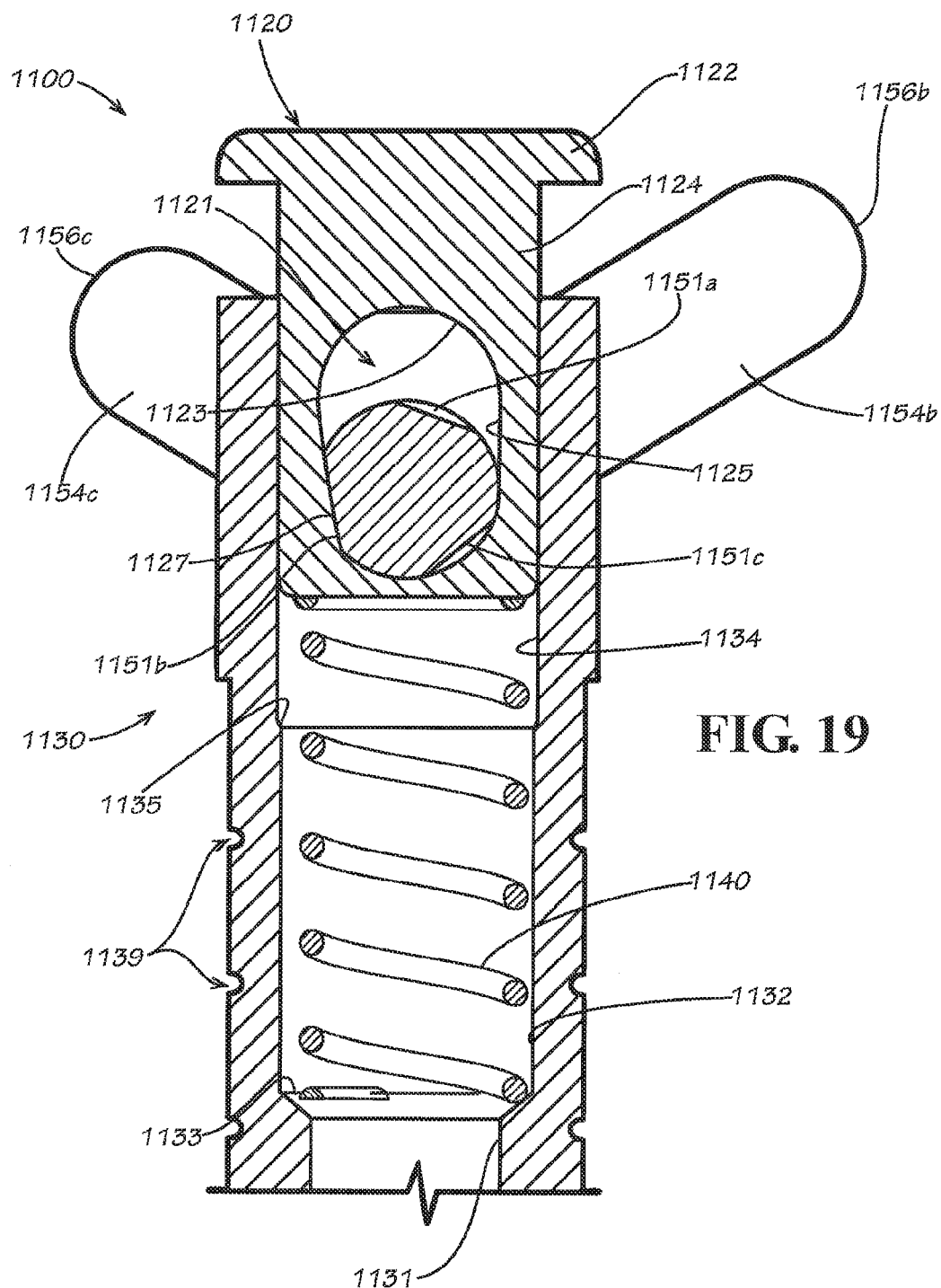
FIG. 19 is a coronal cross-sectional view of the lockable instrument assembly of FIG. 18.

As shown in FIG. 19, a displacement member 1120 is received by at least one receiving portion 1131, 1132, 1134 of the mounting body 1130. The displacement member 1120 may comprise a flange 1122 and an insertion portion 1124 depending from the flange 1122. The insertion portion 1124 is configured to communicate with the at least one receiving portion 1131, 1132, 1134 such that the displacement member 1120 slides freely relative to the mounting body 1130. While the shown embodiment depicts the insertion portion 1124 as a generally smooth cylindrical body that slides within a smooth cylindrical receiving portion 1134, it should be noted that other suitable insertion portion cross-sections may be used, so long as they are operable with the at least one receiving portion 1131, 1132, 1134. For instance, while not shown, the insertion portion 1124 may include one portion of a dovetail joint or track which communicates with a complementary mating portion of said dovetail joint of the at least one receiving portion 1131, 1132, 1134. One of ordinary skill in the art will also appreciate that the at least one receiving portion 1131, 1132, 1134 and the insertion portion 1124 may be of the male or female type, and may be reversed without consequence.

The flange 1122 generally serves to provide a gripping structure to the displacement member 1120; however, it may also serve as a stopping portion to limit movement between the mounting body 1130 and displacement member 1120. Flange 1122 may further serve as a push button or pull handle to easily allow a surgeon to move the displacement member 1120 relative to the mounting body 1130. A transversely-extending shaped aperture 1121 extends through the displacement member 1120, the shaped aperture 1121 comprising a clearance portion 1123 and a locking portion 1125 having one or more rotation prevention features 1127, for instance, flat or straight portions as shown. A shaft 1152 of an adjustment member 1150 is received within said shaped aperture 1121 such that the adjustment member 1150 can be rotated freely and moved along an axis in translation within the aperture 1121 when the adjustment member 1150 is positioned in close proximity to the clearance portion 1123. However, the adjustment member 1150 is prevented from rotating and moving in translation within the shaped aperture 1121 when it is positioned in close proximity to the locking portion 1125 of the shaped aperture 1121. Rotational movement and translational movement of the adjustment member 1150 relative to both the mounting body 1130 and displacement member 1120 is prevented when one or more rotation prevention features 1151a-c located on the adjustment member 1150 engage one or more complementary rotation prevention features 1127 provided within the shaped aperture 1121. A gripping structure 1158 such as a knob or handle may be provided to the adjustment member 1150 in order to facilitate rotation and transverse movement of the adjustment member 1150.

Numerous surgical items may be provided on the adjustment member 1150. For example, the adjustment member 1150 may comprise multiple measuring arms 1154a-c each having a surveying tip 1156a-c. A biasing member 1140 operably provided between the displacement member 1120 and the mounting body 1130 urges the adjustment member 1150 into a normally locked position within the shaped aperture 1121 of the displacement member 1120. While the embodiment shown suggests an instance where displacement member 1120 is "pushed" against a biasing member 1140 (loaded in compression) to unlock the assembly 1100 and move adjustment member 1150, it should be noted that the orientation of the shaped aperture 1121, the geometries of assembly components, the type of biasing member 1140, and the relative connections between the biasing member 1140 mounting body 1130 and displacement member 1120 may obviously be changed, such that the displacement member 1120 can be "pulled" against the biasing member 1140 (loaded in tension) to unlock the assembly 1100 and move the adjustment member 1150. For instance, for the embodiment shown, the displacement member 1120 may be extended to pass through receiving portions 1132, 1131 of the mounting body 1130, so that the displacement member 1120 can be engaged and pulled from a second flange located on the displacement member 1120 at an opposite end of flange 1122.

The instrument assembly 1100 may be adjusted between different locked assembly configurations using rotation prevention features 1127, 1151a-c on both the adjustment member 1050 and the displacement member 1120. In the embodiment shown, three rotation prevention features 1151a-c are spaced evenly around the shaft 1152 of the adjustment member 1150 approximately 120 degrees apart. It should be noted, however, that the circumferential spacings between rotation prevention features 1151a-c may be smaller, larger, odd in number, or even in number without limitation. Moreover, the spacings between rotation prevention features 1151a-c may not be uniform, such that the shaft 1152 is generally asymmetric in one or more cross-sections.

An unlocking force may be applied to the displacement member 1120 to overcome locking forces exerted by biasing member 1140, the unlocking force moving the shaft 1152 of the adjustment member 1150 into the clearance portion 1123 of the shaped aperture 1121. While the adjustment member 1150 is positioned in the clearance portion 1123 of the shaped aperture 1121, it may be rotated to a plurality of angles by applying a rotational force or moment to the adjustment member 1150, for instance, by turning gripping structure 1158. Moreover, while in the clearance portion 1123 of the shaped aperture 1121, the adjustment member 1150 may be moved transversely along its rotational axis by applying linear forces along said axis. When the unlocking force applied to the displacement member 1120 is removed, the biasing member 1140 moves the displacement member 1120 relative to the mounting body 1130 and returns the adjustment member 1150 to the locking portion 1125 of the shaped aperture 1121 where one or more rotation prevention features 1151a-c of the adjustment member 1150 engage one or more complementary rotation prevention features 1127 within the aperture 1121.

FIGS. 14-19 show a single locked assembly configuration where the adjustment member 1150 is positioned and locked at zero degrees of rotation in relation to mounting body 1130 and displacement member 1120. However, those of ordinary skill in the art will appreciate that other locked assembly configurations are possible by applying an unlocking force to the displacement member 1120, rotating the adjustment member 1150 to another angle of rotation, and then removing the unlocking force applied to the displacement member 1120 to lock the adjustment member 1150 in another other angle of rotation.

In some instances, it may be desirable to quickly and easily change the spatial positioning of a first instrumentation component 300 relative to an anatomical landmark or surgical site location 402 of a patient's anatomy 400. For instance, a surgeon may utilize a lockable instrument assembly 1100 to change a superior-inferior positioning of a surgical guide relative to an articular surface (e.g., proximal tibia) in order to control a depth of an anatomical modification to the anatomy 400, such as a bone cut. To do this, a first instrumentation component 300, such as a surgical guide may be coupled with a lockable instrument assembly 1100 such that a surveying tip 1156a of one 1154a of a plurality of measuring arms 1154a-c provided on the adjustment member 1150 rests on said anatomical landmark or surgical site location 402. Depending on one or more physical characteristics of the arm 1154a selected (e.g., a length, height, size, or shape), a spatial relationship between the anatomical landmark or surgical site location 402 and the first instrumentation component 300 is established prior to performing a surgical step. The surgical step may be, for example, a step of performing an anatomical modification such as making a cut, drilling a hole, marking a surface, reaming, broaching, or milling, without limitation. The position of the first instrumentation component 300 may be adjusted relative to the assembly 1100 based on indicia 1139 located on the assembly 1100.

In use, a surgeon engages displacement member 1120 to allow the adjustment member 1150 to rotate freely and/or slide freely along its longitudinal axis relative to the displacement member 1120 and mounting body 1130. In the particular embodiment shown, engagement with the displacement member 1120 comprises "pressing" the displacement member 1120 and thereby applying a force thereto. However, it should be understood that other engagements with the displacement member 1120 relative to the mounting body 1130 may be used to unlock and move the adjustment member 1150. For instance, while not explicitly shown, engagement with the displacement member 1120 may comprise "pulling" the displacement member 1120 relative to the mounting body 1130 to transfer a force thereto. Moreover, engagement with displacement member 1120 may comprise indirectly applying a force to the displacement member 1120 using another device such as a linkage, pivoted lever, or cam and follower to move the displacement 1120 relative to the mounting body 1130.

When the lockable instrument assembly 1100 is unlocked, the surgeon may rotate the adjustment member 1150 to rotationally index and select a single measuring arm 1154a from a plurality of measuring arms 1154a-c provided thereon. In some instances, the selected measuring arm 1154a represents or correlates with a predetermined resection depth, an anatomical measurement, an anatomical reference, a spatial relationship between two surgical instrumentation components, or a spatial relationship between a surgical instrumentation component and an anatomical landmark or surgical site location 402. Steps of identifying and indexing measuring arms 1154a-c may be facilitated by indicia 1111a-c located on the adjustment member 1150. In some instances, indicia may also be provided on the mounting body 1130 or displacement member 1120 to work in conjunction with indicia 1111a-c. For instance, one or more markings such as lines may be provided to the mounting body 1130 or displacement member 1120 which are configured to align with indicia 1111a-c located on the adjustment member 1150. When the surgeon disengages the displacement member 1120 and removes the unlocking force applied thereto, the adjustment member 1150 is subsequently locked (via locking forces exerted by the biasing member 1140) in a predetermined indexed position relative to: the displacement member 1120, the mounting body 1130, the lockable instrument assembly 1100 as a whole, and/or other instrumentation components 300 which may be attached to the assembly 1100. The surveying tip 1156a of the indexed measuring arm 1154a may serve to contact an anatomical landmark or surgical site location 402 of a patient's anatomy 400 (e.g., a tibial sulcus) and directly or indirectly position a surgical instrumentation component 300 (e.g., tibial resection guide) relative to said anatomical landmark or surgical site location 402 and/or other surgical instrumentation components 200 used in the procedure.

FIG. 19 illustrates a step of locking a lockable instrument assembly 1100 in a predetermined locked assembly configuration according to some embodiments. As shown in FIG. 19, adjustment member 1150 is prevented from rotating or translating relative to displacement member 1120 and mounting body 1130 while biasing member 1140 urges at least one 1151b of the multiple rotation prevention features 1151a-c located on the shaft 1152 against at least one rotation prevention feature 1127 located in the shaped aperture 1121. Friction between the rotation prevention features 1127, 1151a-c generally prevents the adjustment member 1150 from rotating and/or translating within the shaped aperture 1121 in the locked assembly configuration. To unlock the assembly 1100 and change the orientation of the adjustment member 1150, a force may be applied to the displacement member 1120 against the biasing member 1140 to move a cross-section of the adjustment member 1150 into a clearance portion 1123 of the shaped aperture 1121 (in a manner similar as shown in FIG. 12). While in the clearance portion 1123, the adjustment member 1150 is permitted to spin freely within the shaped aperture 1121 about its rotational axis (e.g., a longitudinal axis of the shaft portion 1152) and is also permitted to slide transversely along said rotational axis. When the force to the displacement member 1120 is removed, the biasing member 1140 urges the adjustment member 1150 back into a locking portion 1125 of the shaped aperture 1121 such that another one 1151a, 1151c of said one or more rotation prevention features 1151a-c on the shaft 1152 rests against the one or more complementary rotation prevention features 1127 in the aperture 1121. Therefore, the instrument assembly 1100 is adapted to provide at least one locked and unlocked assembly configuration, wherein the unlocked assembly configuration allows rotational and transverse movement of the adjustment member 1150 relative to other portions of the assembly 1100. Such movements of the adjustment member 1150 may be predetermined movements which are based on visualization means 1111a-c and/or a particular surgical step at hand. Translative movements of the adjustment member 1150 along an axis of the shaft 1152 may be infinitesimally small, adjustable movements to suit a particular application. For example, small translative movements may include moving an adjustment member 1150 in tiny increments to position a measuring arm 1154a over the center of a tibial sulcus. The number of locked assembly configurations may be determined in part or in whole by the number of rotation prevention features 1151a-c, the operable working length of shaft 1152 within the shaped aperture 1121, and other design attributes.

FIGS. 20-25 are drawn to a lockable instrument assembly 1200 according to yet other embodiments. The assembly 1200 comprises a biasing member 1240, a displacement member 1220 having a shaped aperture 1221, a mounting body 1230, and an adjustment member 1250 provided within the shaped aperture 1221. Mounting body 1230 receives the displacement member 1220 and may be configured to attach the assembly 1200 to one or more other instrumentation components 300. The biasing member 1240 serves to urge the adjustment member 1250 into a locking 1225 portion of the shaped aperture 1221 having one or more rotation prevention features 1227. In some instances, the adjustment member 1250 may comprise a cam portion 1254 having different peripheral cam geometries 1256a-d provided thereon at various peripheral locations around the cam portion 1254. In the particular instance shown, four peripheral cam geometries 1256a-d are spaced evenly around the cam portion 1254. However, it should be understood that any number of peripheral cam geometries 1256a-d may be used, and that the circumferential spacings between the peripheral cam geometries may vary. The cam portion 1254 may be used with a follower portion to position a first instrumentation component 300 a predetermined distance from a patient's anatomy 400. For example, said follower portion may be an anatomical landmark or surgical site location 402 as shown. Alternatively, while not shown, the follower portion may form part of a surgical instrumentation component, wherein the cam portion 1254 may be used to position the assembly 1200 and instrumentation components 300 attached thereto, a predetermined distance away from said surgical instrumentation component. For example, cam portion 1254 may be used to move a first instrumentation component 300 a specified distance relative to a second instrumentation component 200.

Some peripheral cam geometries (e.g., geometry 1256d) may be configured to position an instrumentation component 300 a greater distance from an anatomical landmark or surgical site location 402 than other cam geometries (e.g., cam geometry 1256a). In use, a single geometry 1256a which is configured to position an instrumentation component 300 at a desired location relative to the surgical site location 402 is selected with the help of indicia 1211a-d. The selected geometry 1256a is indexed by applying a force to the displacement member 1220, unlocking the assembly 1200, rotating and/or translating the adjustment member 1250 until said selected geometry 1256a is properly located with respect to the assembly 1200 and landmark 402, and then removing the force to lock the assembly 1200 in a locked assembly configuration. Contacting different cam geometries 1256a-d with the same surgical site location 402 may help position an instrumentation component 300 at different spatial locations relative to said location 402. The assembly 1200 may find particular utility in surgical procedures where re-cuts and other duplicative anatomical modifications are necessary. In such instances, the anatomical landmark or surgical site location 402 may comprise a previously made bone cut or other previously made anatomical modification.

Fine rotational and/or translational movement of the adjustment member 1250 is permitted relative to the rest of the assembly 1200 when the assembly is in an unlocked assembly configuration. However, rotational and/or translational movement of the adjustment member 1250 relative to the rest of the assembly 1200 is prevented when the assembly is in a locked assembly configuration. In some instances, the instrument assembly 1200 may form a portion of sizing guide, for example, a femoral or tibial sizing guide for use in a total knee arthroplasty (TKA) procedure. The assembly 1200 may be used to move a first instrumentation component 300 (e.g., a surgical guide for cutting, reaming, drilling, milling, or broaching) relative to an anatomical landmark or surgical site location 402. The assembly 1200 may also be used to move a first instrumentation component 300 relative to another instrumentation component 200.

Adjustment member 1250 may be provided with numerous surgical items and the novel locking features of the lockable instrument assemblies disclosed herein may be used in combination with many surgical instrumentation components including, but not limited to: intramedullary rods, extramedullary rods, reamers and reaming devices, surgical impactors and impacting devices, mounting apparatuses, cutting blocks, cutting jigs, cutting tools, alignment guides (e.g., varus/valgus, flexion/extension, internal/external rotation, anterior-posterior, superior-inferior, and medial-lateral), broaching devices, milling devices, external fixation frames, pin locator guides, targeting devices, referencing tools for use with computer-assisted surgical (CAS) navigation systems, and combinations thereof.

Figure 20:
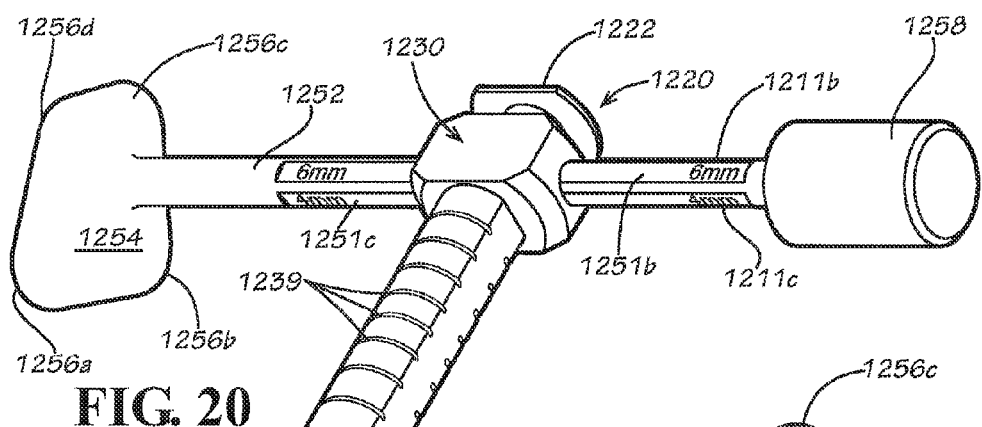
FIG. 20 is a perspective view of a lockable instrument assembly according to other embodiments.
Figure 21:
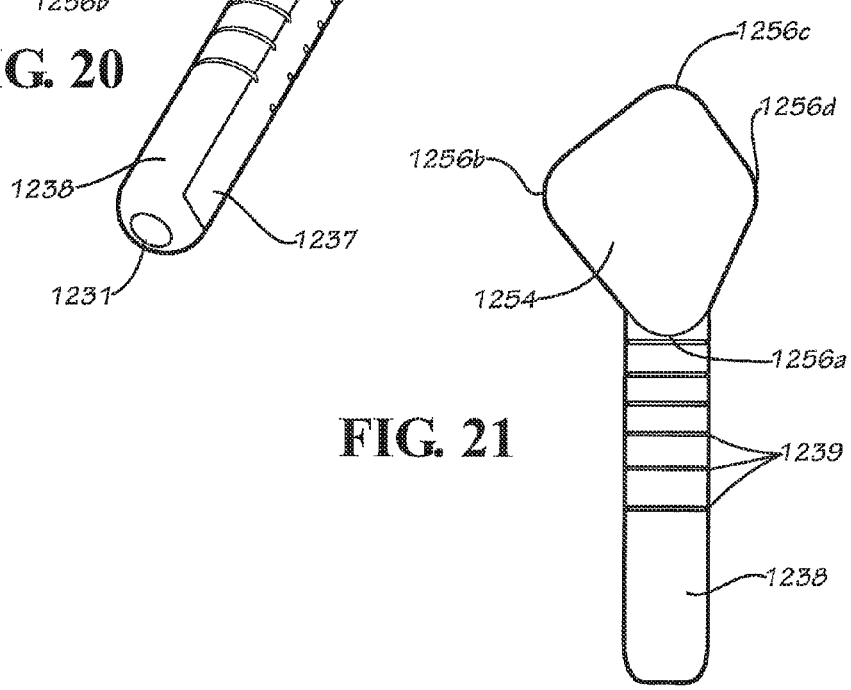
FIG. 21 is a frontal view of the lockable instrument assembly of FIG. 20.
Figure 22:
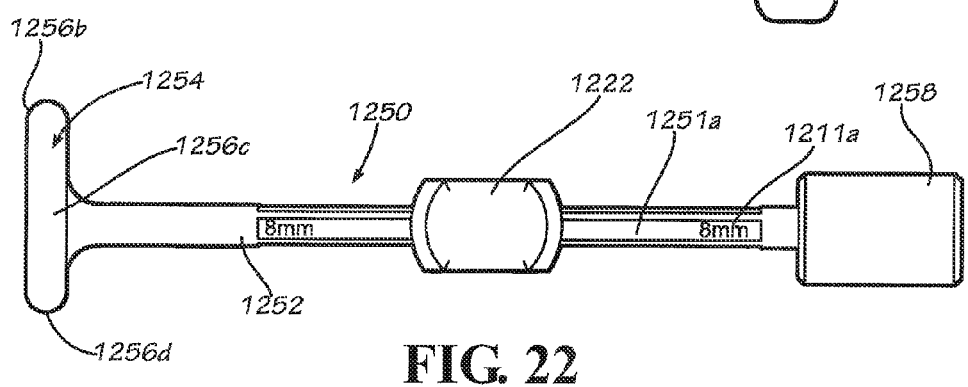
FIGS. 22 and 23 are top and bottom views of the lockable instrument assembly of FIG. 20, respectively.
Figure 23:
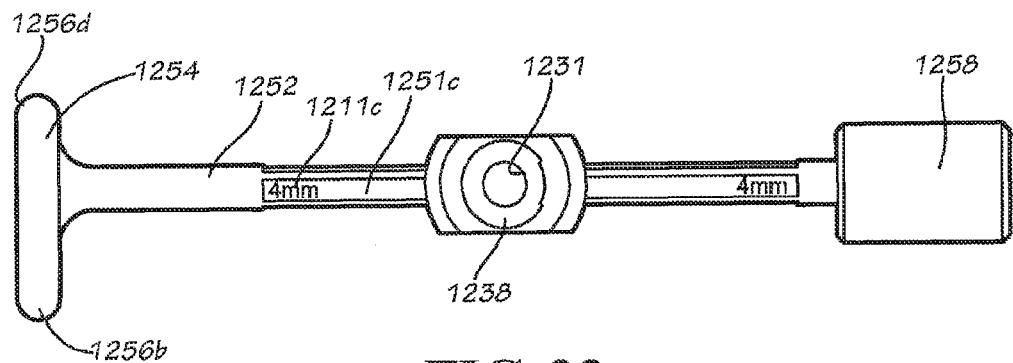
Figure 24:
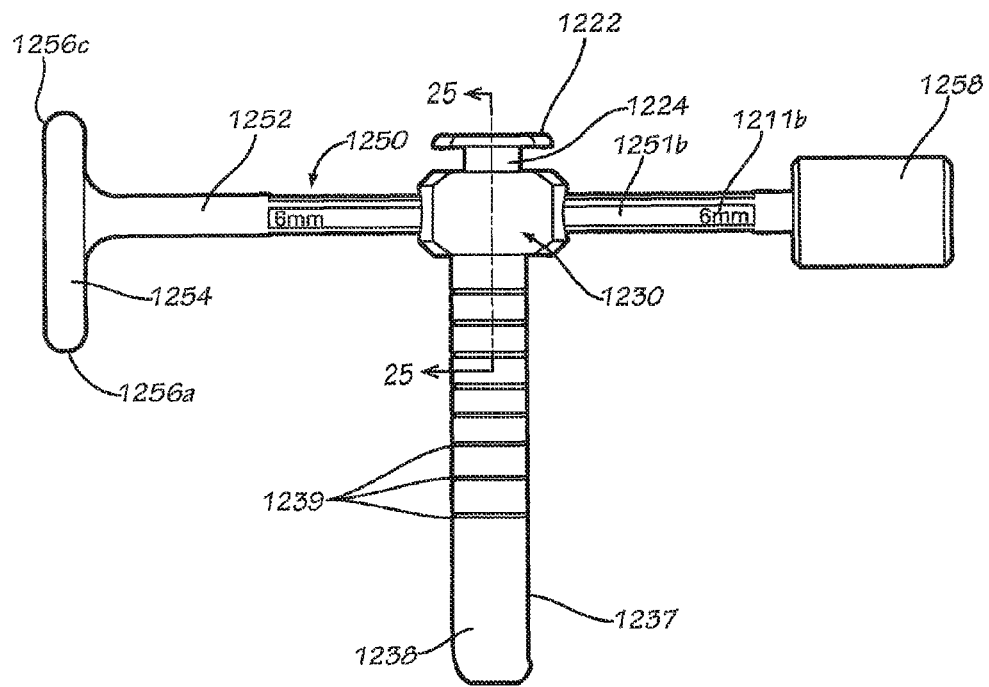
FIG. 24 is a side view of the lockable instrument assembly of FIG. 20.
Figure 25:
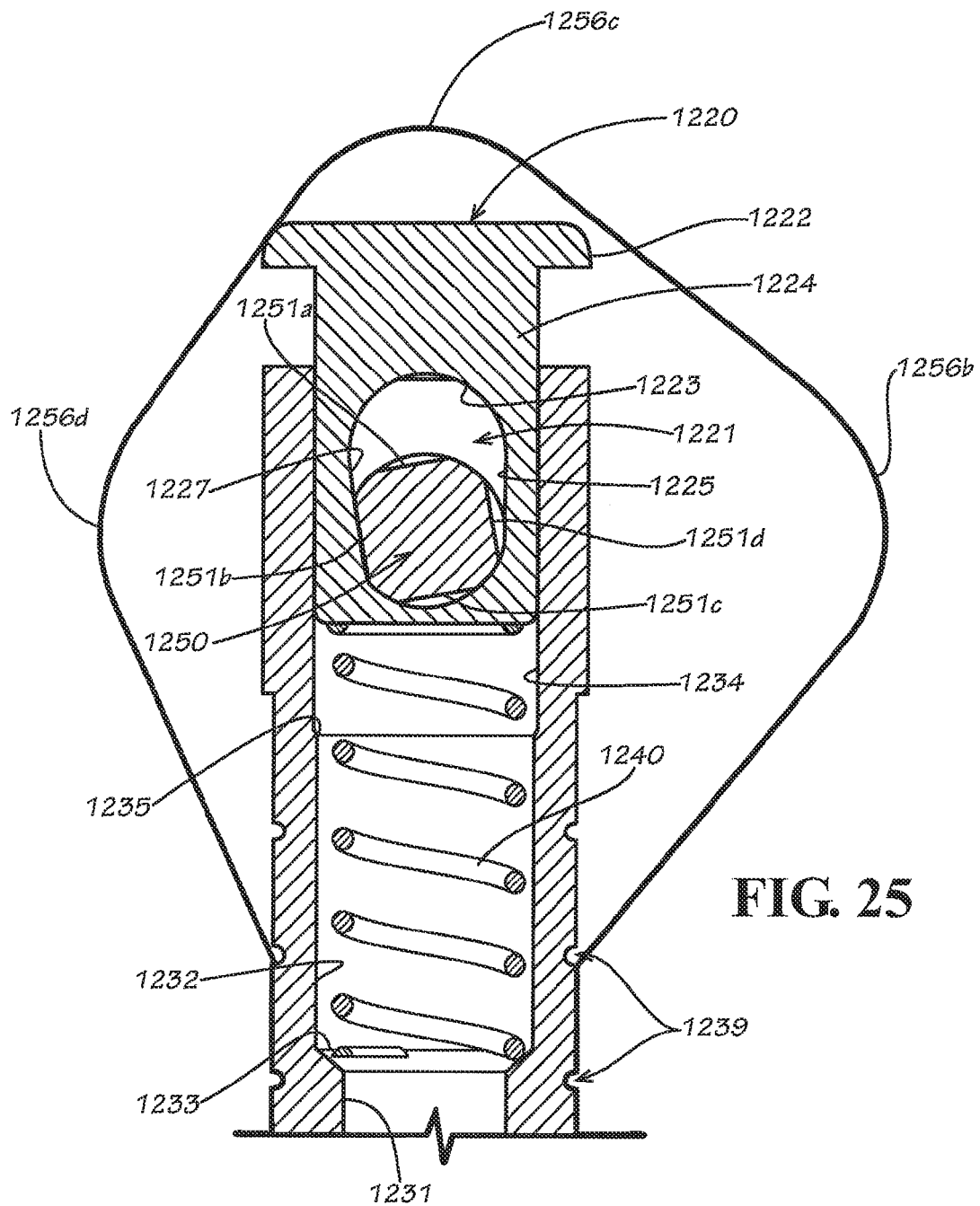
FIG. 25 is a coronal cross-sectional view of the lockable instrument assembly of FIG. 24; and, FIGS. 26 and 27 are perspective views demonstrating practical utilities of lockable instrument assemblies.

Turning now to FIG. 20, a perspective view of an instrument assembly 1200 is shown. The assembly 1200 comprises a mounting body 1230 having a housing portion 1236, a mounting portion 1238, and at least one receiving portion 1231, 1232, 1234 configured to receive a displacement member 1220 in a sliding moveable fashion. One or more stopping portions 1233, 1235 may also be provided to mounting body 1230 for limiting movement between the displacement member 1220 and mounting body 1230. The one or more stopping portions 1233, 1235 may be formed by geometric changes between receiving portions 1231, 1232, 1234, and may comprise, for instance, a step or a shelf portion as shown. Mounting surfaces 1237 such as flat areas may be provided on the mounting portion 1238 and may serve as a rotation prevention feature between the mounting body 1230 and a first instrumentation component 300. One or more location features 1239 may also be provided to the mounting body 1230 to align a first instrumentation component 300 with the assembly 1200. As shown in FIG. 25, a displacement member 1220 such as a button or a plunger may be configured to communicate with the at least one receiving portion 1234 of the mounting body 1230, and movement of the displacement member 1220 may be limited by a stopping portion 1235. One or more stopping portions 1233 may also serve to mount or prevent movement of a biasing member 1240 relative to the mounting body 1230 as will be discussed hereinafter.

The displacement member 1220 may comprise a flange 1222 and an insertion portion 1224 which communicates with the at least one receiving portion 1234. A transversely-extending shaped aperture 1221 having a non-circular cross-sectional profile extends through the displacement member 1220, said shaped aperture 1221 comprising a clearance portion 1223 and a locking portion 1225 having one or more rotation prevention features 1227. A shaft 1152 of an adjustment member 1250 is received within said shaped aperture 1221 such that the adjustment member 1250 can be rotated freely and slide transversely within the shaped aperture 1221 when it is positioned adjacent to the clearance portion 1223, but cannot rotate or move transversely within the aperture 1221 when it 1250 is positioned adjacent to locking portion 1225. Rotation of the adjustment member 1250 relative to the mounting body 1230 and displacement member 1220 is prevented when one or more rotation prevention features 1251a-d located on the shaft portion 1252 of the adjustment member 1250 engage one or more complementary rotation prevention features 1227 provided within the shaped aperture 1221. A gripping structure 1258 such as a knob, handle, lever, outer torque application surface (hexagonal drive head), or inner torque application surface (e.g., hexagonal drive recess) may be provided on the adjustment member 1250 to facilitate rotation and/or translation of the adjustment member 1250 relative to the mounting body 1230 and displacement member 1220. A biasing member 1240 is operable between the mounting body 1230 and displacement member 1220 and configured to urge the shaft 1252 of the adjustment member 1250 in a normally-locked position within the shaped aperture 1221. While the biasing member 1240 is shown as a compression-type coil spring, other means for biasing the shaft portion 1252 into a locked assembly configuration may be provided, including, but not limited to: resilient materials, leaf springs, torsion springs, tension springs, elastics, permanent magnets, and other force-producing means.

The lockable instrument assembly 1200 may be adjusted to provide different locked assembly configurations for various applications. The different locked assembly configurations are generally made possible by providing multiple rotation prevention features 1251a-c on the adjustment member 1250. In the embodiment shown, four rotation prevention features 1251a-d are spaced evenly around the circumference of shaft portion 1252 of the adjustment member 1250, each being spaced approximately 90 degrees apart. It should be noted however, that the spacing between the one or more rotation prevention features 1251a-d can be smaller, larger, odd in number, or uneven in number. Moreover, depending on the surgical application, the one or more rotation prevention features 1251a-d may be spaced unevenly around the shaft 1252 such that the adjustment member 1250 is asymmetric in at least one cross-section. An unlocking force applied to the displacement member 1220 moves the adjustment member 1250 into the clearance portion 1223 of the shaped aperture 1221 against locking forces exerted by biasing member 1240.

While the shaft 1252 is in the clearance portion 1223 of the shaped aperture 1221, it may be rotated to one of a plurality of angles and/or may be slid along its axis in a transverse direction through the shaped aperture 1221 by applying a moment, rotational force, or longitudinal force to the adjustment member 1250, for example, through gripping structure 1258. When the unlocking force applied to the displacement member 1220 is removed, the biasing member 1240 returns the shaft 1252 to a locking portion 1225 of the shaped aperture 1221 where the one or more rotation prevention features 1251a-d of the adjustment member 1250 engage the one or more complementary rotation prevention features 1227 within the shaped aperture 1221. Frictional forces prevent further rotation and translation of the adjustment member 1250 with respect to the assembly 1200 when the assembly is in a locked assembly configuration.

Figure 26:
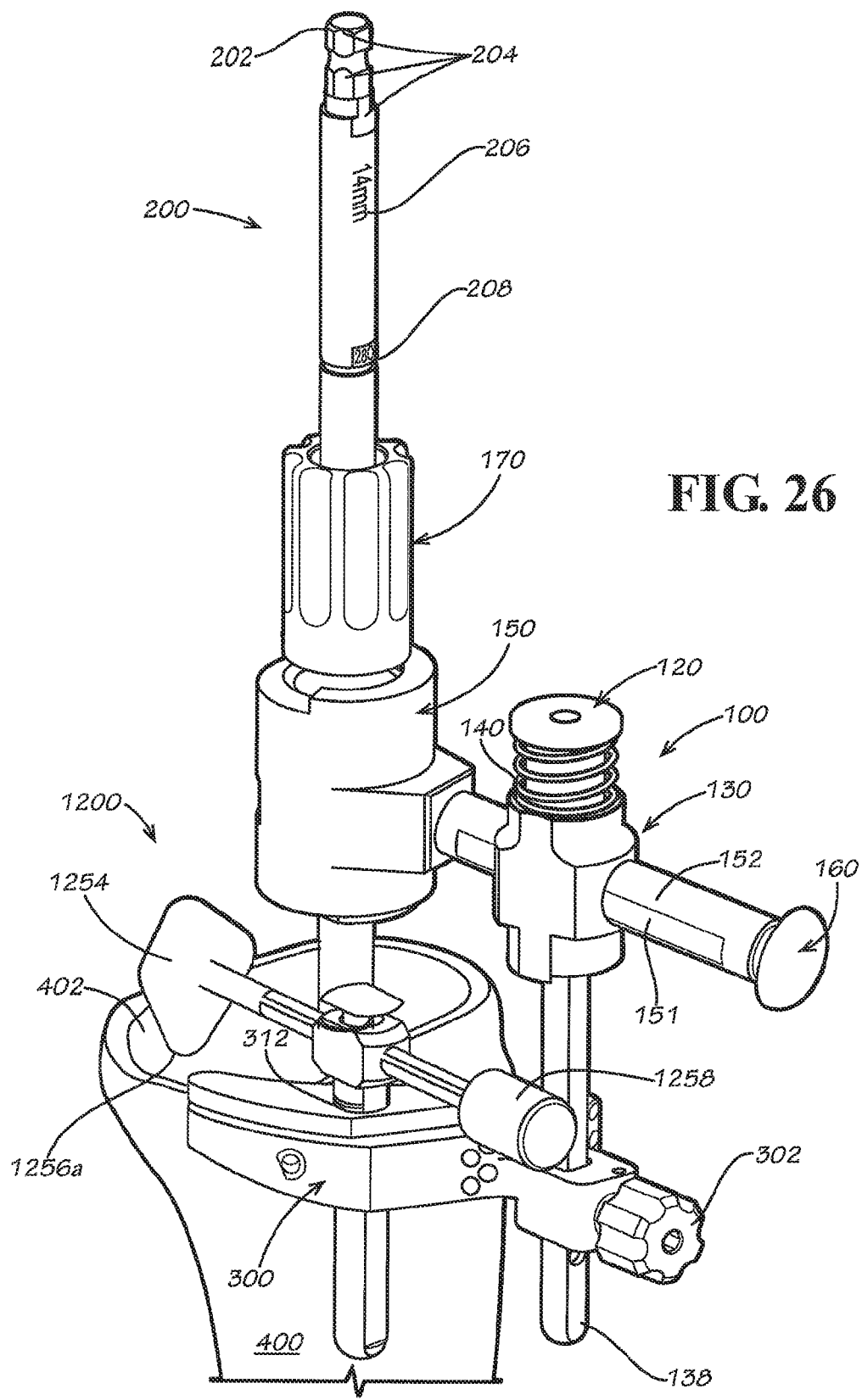

While FIGS. 20-25 show only one of many possible locked configurations, those of ordinary skill in the art will appreciate the other configurations possible. In the particular embodiment shown in FIGS. 20-25, the adjustment member 1250 may be locked in four different rotational positions in a first rotational degree of freedom. However, numerous additional locked assembly configurations are possible since the adjustment member 1250 may also be moved various amounts in a second translative degree of freedom. In some instances, it may be desirable for surgical staff to quickly and efficiently change the relative positioning of a first instrumentation component 300 relative to a patient's anatomy 400 or a second instrumentation component 200. For example, a lockable instrument assembly 1200 may help a surgeon selectively utilize different peripheral geometries 1256a-d as a means for incrementally positioning or repositioning a tide mark, a bone cut, a bone re-cut, a peg hole, a pin hole, a keel punch, or a resection surface. FIG. 26 illustrates one example where a peripheral geometry 1256a can be used to position a resection guide a specified distance from a proximal tibial plateau.

In use, a surgeon may move the displacement member 1220 against biasing forces exerted by biasing member 1240 in order to allow the adjustment member 1250 to rotate and translate freely. The surgeon may then index the adjustment member 1250 to select a particular geometry 1256a from a plurality of geometries 1256a-d and move the adjustment member 1250 in translation so that the selected geometry 1256a is located adjacent to a desired anatomical feature or properly positioned relative to other surgical instruments. Geometries 1256b-d may be representative of different surgical instrument positions. Indexing, positioning, and locking the adjustment member 1250 can be facilitated by indicia 1211a-d located on the device. When the surgeon removes the unlocking force(s) from the displacement member 1220, the displacement member 1220 returns to its resting state and the adjustment member 1250 and corresponding selected geometry 1256a are locked in a predetermined locked position relative to the body 1220, mounting body 1230, and/or other surgical instrumentation components 300 which may be attached to the assembly 1200. The selected geometry 1256a may contact a surface portion 402 of a patient's anatomy 400 such as a proximal tibia sulcus in order to directly or indirectly position a surgical instrumentation component 300, such as a tibial resection guide. Positioning of the component 300 may be done in relation to portions of a patient's anatomy, or in relation to other surgical instrumentation components 200 used in the procedure. In some instances, lockable instrument assemblies 1200 may be used in computer assisted surgical (CAS) procedures in order to control fine adjustments to the positioning of surgical instruments having fiducial markers thereon.

FIG. 25 illustrates a step of locking a lockable instrument assembly 1200 according to some embodiments. As shown in FIG. 25, adjustment member 1250 is prevented from rotation and translation relative to mounting body 1230 and displacement member 1220, since biasing member 1240 urges at least one 1251b of said one or more rotation prevention features 1251a-c on the shaft 1252 against one or more rotation prevention features 1227 within the aperture 1221. Frictional forces between the one or more rotation prevention features 1227, 1251b prevents relative movement between the adjustment member 1250, mounting member 1230, and displacement member 1220. To unlock the assembly 1200, a force is applied to the displacement member 1220 to move a cross-section of the adjustment member 1250 into a clearance portion 1223 of the shaped aperture 1221 in a manner similar to that shown in FIG. 12. Moving the adjustment member 1250 into the clearance portion 1223 allows the adjustment member 1250 to spin freely in the shaped aperture 1221 about a rotational axis (e.g., a longitudinal axis of the shaft portion 1252), and also allows the member 1250 to slide transversely along said axis to position a surgical instrumentation component 300 relative to a patient's anatomy 400, 402 and/or other surgical instrumentation. When the force is removed, the biasing member 1240 returns the shaft portion 1252 of the adjustment member 1250 back to the locking portion 1225 of the shaped aperture 1221 such that the same 1251b or another 1251a,c,d of said one or more rotation prevention features 1251a-d on the shaft 1252 rests against the one or more rotation prevention features 1227 in the aperture 1221. Therefore, the lockable instrument assembly 1200 is adapted to provide at least one locked assembly configuration and at least one unlocked assembly configuration, wherein infinitesimal rotational and translational adjustment to the adjustment member 1250 position may be made in said unlocked assembly configuration. The number of locked assembly configurations possible may be governed in part or in whole by the number of rotation prevention features 1227, 1251a-d, the operable length of the shaft 1252, and other design attributes of the assembly 1200.

It should be understood that while the biasing member 1240 is depicted as a compression or coil spring, any known means for normally biasing the adjustment member 1250 into a locking portion 1225 of a shaped aperture 1221 may be used including, but not limited to: resilient materials, leaf springs, torsion springs, tension springs, elastics, permanent magnets, and other force-producing means.

Figure 27:
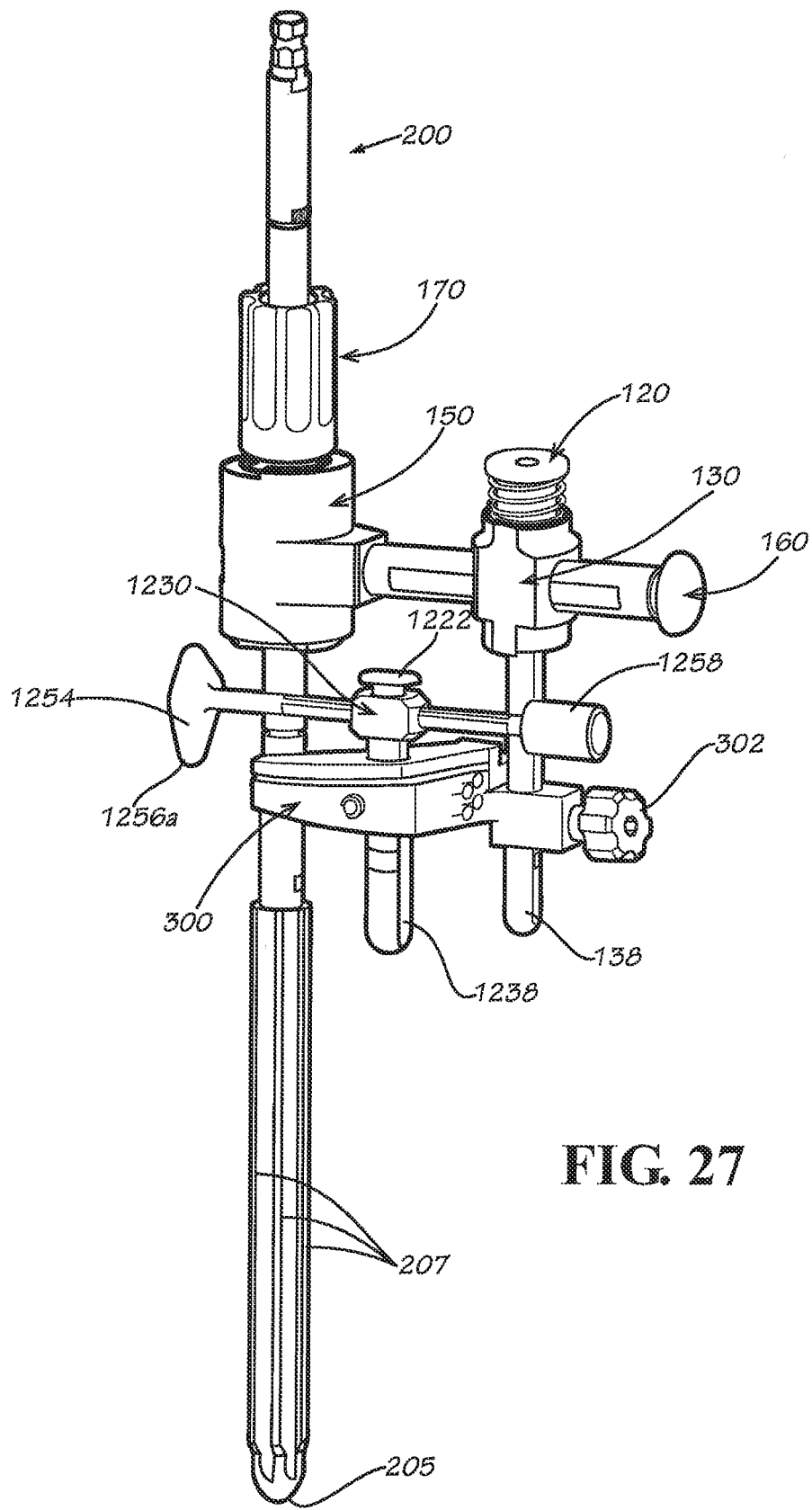

FIGS. 26 and 27 show some possible uses for the instrument assemblies 100, 1000, 1100, 1200 described herein. For instance, a first lockable instrument assembly 100 may be used to position a first surgical instrumentation component 300 in a rotational relationship with respect to a second surgical instrumentation component 200 or a portion 402 of a patient's anatomy. The first lockable instrument assembly 100 may further serve to position a first instrumentation component 300 in a first translational relationship (e.g., in a linear degree of freedom) with respect to a second surgical instrumentation component 200 or a portion of a patient's anatomy 400. In the particular instance shown in FIGS. 26 and 27, said first translational relationship generally extends in an anterior to posterior direction within a transverse plane, however other directions are envisaged.

The sleeve 110, collet 190, knob 170, and actuator 180 further help position the first surgical instrumentation component 300 in a second translational relationship which is different from said first translational relationship. In the instance shown in FIGS. 26 and 27, the second translational relationship generally extends in a superior-inferior direction in a coronal or sagittal plane generally perpendicular to the first translational relationship. A second lockable instrument assembly 1200 may be provided in conjunction with said first lockable instrument assembly 100 to provide fine tuned positional adjustments or measurements in at least one of said first and second translational relationships. In the particular embodiments shown, the second lockable instrument assembly 1200 provides a fine tuned positional adjustment of the first surgical instrumentation component 300 in said second translational relationship. In use, surgical staff may loosen or otherwise disengage securing means 302, allowing a selected peripheral geometry 1256*a* to contact a desired anatomical landmark or surgical site location 402. A surgical instrumentation component 300 may be positioned relative to anatomy 400, 402 and other surgical instrumentation components using the second lockable instrument assembly 1200, and then the securing means 302 may be engaged or tightened to set the position of the component 300.

FIG. 28 is an alternative embodiment which uses a "pulling" force on a displacement member 1320 to unlock a lockable instrument assembly 1300, rather than a "pushing" force. The assembly 1300 is placed in an unlocked assembly configuration by pulling on a gripping portion 1322 provided on a displacement member 1320, against locking forces exerted by biasing member 1340. When the locking forces exerted by biasing member 1340 are overcome by the pulling force applied to the displacement member 1320, an adjustment member 1350 moves into a clearance portion 1323 of a shaped aperture 1321. A stopping portion 1335 is provided to a mounting body 1330 to limit the relative movement of the displacement member 1320. Stopping portion 1335 may also help align the adjustment member 1350 with the clearance portion 1323 when the displacement member 1320 is fully displaced with respect to the mounting body 1330. A second stopping portion 1333 may also be provided in order to hold biasing member 1340 immoveable relative to the mounting body 1330. Alternatively, the biasing member 1340 may be secured to the mounting body 1330 and displacement member 1320 by other attachment means, for example, by placing each end of the biasing member 1340 in a respective receiving portion (e.g., hole or groove) located on the mounting body 1330 or displacement member 1320. In the unlocked assembly configuration, the rotational and translative position of the adjustment member 1350 may be adjusted. Once the adjustment member 1350 is positioned in a desired rotational and transverse location, the gripping portion 1322 is released and the adjustment member 1350 moves adjacent to a locking portion 1325 of the shaped aperture 1321 where at least one 1351*a-c* rotation prevention feature on the adjustment member 1350 engage at least one complementary rotation prevention feature 1327 of the shaped aperture 1321.

FIG. 29 illustrates an alternative embodiment of a lockable instrument assembly 1400, wherein an insertion portion 1436 of a mounting body 1430 is received within a receiving portion 1426 of a displacement member 1420. The insertion 1436 and receiving 1426 portions may be provided in any configuration, for example, as portions of a male and female connection, portions of a dovetail joint connection, portions of a sliding track configuration, portions of a telescoping connection, or the like. In some instances, as the one shown in FIG. 29, the displacement member 1420 may also comprise an insertion portion 1424 which is respectively received in a receiving portion 1434 of the mounting body 1430.

The mounting body 1430 and/or the displacement member 1420 may further comprise at least one stopping portion 1427, 1435 to limit relative movement between the displacement member 1420 and the mounting body 1430. The at least one stopping portion 1435, 1437 may additionally serve to align the shaft 1452 of an adjustment member 1450 with a clearance portion 1423 of a shaped aperture provided on the displacement member 1420, when the displacement member 1420 is fully displaced with respect to the mounting body 1430. A stopping portion 1426' may also be provided at the receiving portion 1426 of the displacement member 1420, in order to hold biasing member 1440 immoveable relative to the displacement member 1420.

FIGS. 30-32 illustrate the step of unlocking an alternative embodiment of a lockable instrument assembly 1500. The assembly 1500 comprises a displacement member 1520 having a flange 1522, an insertion portion 1524, and an aperture 1521 suitable for receiving a shaft of an adjustment member 1550 therein. The aperture 1521 is complementary to a profile of the adjustment member 1550, such that the adjustment member 1550 is generally rotatable within and slideable in translation along its axis. A mounting body 1530 having at least one receiving portion 1532, at least one stopping portion 1534, 1537, and a transversely-extending shaped aperture 1531, receives the displacement member 1520. The shaped aperture 1531 has a locking portion 1533 and a clearance portion 1535, the locking portion 1533 comprising one or more rotation prevention features 1537 which are complementary to one or more rotation prevention features 1551*a-d* provided on the shaft of the adjustment member 1550. A biasing member 1540 operably provided between the displacement member 1520 and mounting body 1530 normally urges the one or more rotation prevention features 1551*a-d* provided on the shaft of the adjustment member 1550 against the one or more complementary rotation prevention features 1537 provided on the shaped aperture in a locked assembly configuration as shown in FIGS. 30 and 31.

As shown in FIG. 32, the assembly 1500 may be unlocked by providing an unlocking force to the displacement member 1520 to move the displacement member 1520 relative to the mounting body 1550 against locking forces provided by biasing member 1540. This places the adjustment member 1550 into the clearance portion 1533 of the shaped aperture so that it may be rotated and/or translated with respect to the rest of the assembly 1500. After the adjustment member 1550 is translated and/or rotated to a preferred angle of rotation, the unlocking force to the displacement member 1520 may be released to place the assembly 1500 into a locked assembly configuration. In the embodiment shown in FIGS. 30-32, the adjustment member 1550 is configured to move in three degrees of freedom when the assembly 1500 is in an unlocked assembly configuration, the three degrees of freedom including: rotation along an axis of the adjustment member 1550, translation along an axis of the adjustment member 1550, and lateral translation along the length of the oblong shaped aperture 1533.

It should be noted that while the lockable instrument assemblies 100, 1000, 1100, 1200, 1300, 1400, 1500 and their components are shown and described for use with tibial knee instrumentation, it is acknowledged that such assemblies and components thereof will find equal utility in femoral knee instrumentation, as well as surgical instrumentation used in surgeries of the hip, shoulder, elbow, spine, extremities, and craniofacial areas, as well as trauma reconstruction applications. The assemblies 100, 1000, 1100, 1200, 1300, 1400, 1500 may also find utility in surgical instrumentation requiring a quick release adapted to provide instant locked and unlocked assembly configurations, particularly where one or more rotational and/or translational adjustments between surgical instrumentation components are required. Lastly, features of the assemblies 100, 1000, 1100, 1200, 1300, 1400, 1500 described herein may provide advantages where strong locking characteristics are desired.

It should also be noted that the adjustment members 150, 1050, 1150, 1250, 1350, 1450, 1550 described herein may comprise shortened shafts, shafts having limited operable lengths of engagement for communicating with a shaped aperture 121, 1021, 1121, 1221, 1321, 1421, or shafts having translation-limiting portions such as flanges directly adjacent to either side of the shaped aperture 121, 1021, 1121, 1221, 1321, 1421, 1531 in order to substantially prevent translation of the adjustment member 150, 1050, 1150, 1250, 1350, 1450, 1550 within the shaped aperture 121, 1021, 1121, 1221, 1321, 1421, 1531 but still allow rotation of the adjustment member 150, 1050, 1150, 1250, 1350, 1450, 1550 within the shaped aperture 121, 1021, 1121, 1221, 1321, 1421, 1531.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The invention claimed is:

1. A device for use in a medical procedure, the device comprising:
   a body;
   a displacement member slideably engaged with and moveable with respect to said body;
   a shaped aperture provided on one of the body or the displacement member, the shaped aperture having a first shaped portion and a second shaped portion, the first shaped portion including an inner surface with a cross-section having a non-circular segment;
   an adjustment member disposed within the shaped aperture; and
   a biasing member;
   wherein contact of the adjustment member with the non-circular segment prevents the adjustment member from being at least one of rotated or translated relative to the body or displacement member;
   wherein the adjustment member is capable of being at least one of rotated or translated relative to the body or displacement member when the adjustment member is positioned adjacent to the second shaped portion; and
   wherein the biasing member is configured to normally position the adjustment member adjacent to said first shaped portion.

2. The device of claim 1, wherein the first shaped portion comprises one or more rotation prevention features that prevent rotation of the adjustment member relative to the body or displacement member.

3. The device of claim 2, wherein the adjustment member further comprises one or more rotation prevention features which are complementary to the one or more rotation prevention features of the first shaped portion.

4. The device of claim 2, wherein said one or more rotation prevention features comprises at least one of a non-arcuate portion, a line segment, a flat portion, a straight portion, or a linear portion.

5. The device of claim 2, wherein said one or more rotation prevention features of the first shaped portion comprises a protuberance or a recess.

6. The device of claim 1, wherein the first shaped portion comprises an anti-rotation profile which complements an anti-rotation profile of the adjustment member.

7. The device of claim 1, wherein the aperture is generally D-shaped, ovoid, or tapered in cross-section.

8. The device of claim 1, wherein the aperture is larger in cross-section adjacent the second shaped portion and smaller in cross-section adjacent the first shaped portion.

9. The device of claim 1, wherein the aperture is asymmetric in cross-section.

10. The device of claim 1, wherein at least one of the body and the displacement member comprises a means for limiting relative movement between the body and the displacement member, and wherein the adjustment member is positioned adjacent to either the first shaped portion or the second shaped portion when movement between the body and the displacement member is prevented by said means.

11. The device of claim 1, wherein the adjustment member comprises a cam having one or more peripheral geometries.

12. The device of claim 1, wherein the adjustment member comprises a measuring device.

13. The device of claim 1, wherein the adjustment member has a moveable activation member received therein.

14. The device of claim 1, wherein the adjustment member is normally positioned adjacent the first shaped portion by forces exerted by the biasing member.

15. The device of claim 1, wherein the body comprises means for mounting a surgical guide for marking, cutting, drilling, reaming, milling, burring, impacting, or broaching.

16. The device of claim 1, wherein the second shaped portion is located opposite the first shaped portion.

17. A device for use in a medical procedure, the device comprising:
   a body;
   a displacement member slideably engaged with and moveable with respect to said body;
   a shaped aperture provided on one of the body or the displacement member, the shaped aperture having a longitudinal through axis and a non-circular annular profile along the entire extent of the longitudinal through axis, the non-circular annular profile defined by a first shaped portion and a second shaped portion;
   an adjustment member disposed within the shaped aperture; and
   a biasing member;
   wherein the adjustment member is prevented from being at least one of rotated or translated relative to the body or displacement member when the adjustment member is positioned adjacent to the first shaped portion;
   wherein the adjustment member is capable of being at least one of rotated or translated relative to the body or displacement member when the adjustment member is positioned adjacent to the second shaped portion; and
   wherein the biasing member is configured to normally position the adjustment member adjacent to said first shaped portion.

18. The device of claim 17, wherein the adjustment member is prevented from being rotated relative to the body or displacement member when the adjustment member is positioned adjacent to the first shaped portion, and the rotation is prevented by engagement of the adjustment member with a surface within the shaped aperture.

19. The device of claim 17, wherein engagement of the first shaped portion with the adjustment member prevents rotation and translation of the adjustment member relative to the body or the displacement member when the adjustment member is positioned adjacent to the first shaped portion.

20. The device of claim 17, wherein the adjustment member can rotate relative to the displacement member or the body when the adjustment member is adjacent the second shaped portion.

21. A device for use in a medical procedure, the device comprising:
   a body;
   a displacement member slideably engaged with and moveable with respect to said body;
   a shaped aperture provided on one of the body or the displacement member, the shaped aperture having a first shaped portion and a second shaped portion;
   an adjustment member disposed within the shaped aperture and including a shaft region having a continuous longitudinal extent; and
   a biasing member;
   wherein the adjustment member is prevented from being translated relative to the body or displacement member when the shaft region of the adjustment member is positioned adjacent to the first shaped portion at any relative position of the shaft region and the first shaped portion;
   wherein the adjustment member is capable of being at least one of rotated or translated relative to the body or displacement member when the adjustment member is positioned adjacent to the second shaped portion; and
   wherein the biasing member is configured to normally position the adjustment member adjacent to said first shaped portion.

22. A device for use in a medical procedure, the device comprising:
   a body;
   a displacement member slideably engaged with and moveable with respect to said body;
   a shaped aperture provided on one of the body or the displacement member, the shaped aperture having a first shaped portion and a second shaped portion, the first shaped portion including a non-circular cross-section;
   an adjustment member disposed within the shaped aperture; and
   a biasing member;
   wherein the adjustment member is prevented from being at least one of rotated or translated relative to the body or displacement member when the adjustment member is positioned adjacent to the first shaped portion and in contact with the non-circular cross-section of the first shaped portion;
   wherein the adjustment member is capable of being rotated relative to the body or displacement member when the adjustment member is positioned adjacent to the second shaped portion; and
   wherein the biasing member is configured to normally position the adjustment member adjacent to said first shaped portion.

\* \* \* \* \*